US011666655B2

(12) United States Patent
Rathore et al.

(10) Patent No.: US 11,666,655 B2
(45) Date of Patent: Jun. 6, 2023

(54) FORMULATION FOR STABILIZING BIO-THERAPEUTICS

(71) Applicant: Indian Institute of Technology, Delhi, New Delhi (IN)

(72) Inventors: Anurag Singh Rathore, New Delhi (IN); V. Haridas, New Delhi (IN); Rohit Bansal, New Delhi (IN); Soumili Chattopadhyay, New Delhi (IN); Sameer Dhawan, New Delhi (IN)

(73) Assignee: Indian Institute of Technology, Delhi, New Delhi (IN)

( * ) Notice: Subject to any disclaimer, the term of this patent is extended or adjusted under 35 U.S.C. 154(b) by 1098 days.

(21) Appl. No.: 16/315,360

(22) PCT Filed: Jun. 8, 2017

(86) PCT No.: PCT/IN2017/050233
§ 371 (c)(1),
(2) Date: Jan. 4, 2019

(87) PCT Pub. No.: WO2018/096552
PCT Pub. Date: May 31, 2018

(65) Prior Publication Data
US 2020/0179523 A1 Jun. 11, 2020

(30) Foreign Application Priority Data
Nov. 28, 2016 (IN) .............................. 201611040627

(51) Int. Cl.
| | |
|---|---|
| *A61K 47/60* | (2017.01) |
| *C08L 101/00* | (2006.01) |
| *A61K 39/395* | (2006.01) |

(52) U.S. Cl.
CPC ........ *A61K 47/60* (2017.08); *A61K 39/39591* (2013.01); *C08L 101/005* (2013.01)

(58) Field of Classification Search
CPC .. A61K 47/60; A61K 39/39591; A61K 45/06; A61K 38/00; A61K 47/26; A61K 9/0019; C07K 16/00; C08G 69/10; C08L 77/04; C08L 89/00; C08L 101/005
See application file for complete search history.

(56) References Cited

U.S. PATENT DOCUMENTS

| | | | |
|---|---|---|---|
| 4,457,916 A | 7/1984 | Hayashi et al. | |
| 5,730,969 A | 3/1998 | Hora et al. | |
| 2003/0077295 A1* | 4/2003 | Malik .................... | C08G 69/02 424/400 |
| 2007/0238654 A1* | 10/2007 | Deschatelets ...... | G01N 33/6872 623/4.1 |
| 2010/0292148 A1* | 11/2010 | Krippner ................. | A61P 11/10 514/10.7 |

FOREIGN PATENT DOCUMENTS

| | | |
|---|---|---|
| JP | 2009153469 A | 7/2009 |
| WO | 9003784 A1 | 4/1990 |

OTHER PUBLICATIONS

E.R. Gillies et al., "Dendrimers and dendritic polymers in drug delivery," Reviews, Drug Discovery Today, vol. 10, No. 1, published Jan. 2005, pp. 35-43.*
V. Haridas et al., "Designer peptide dendrimers using click reaction," Tetrahedron 67, published Jan. 13, 2011, pp. 1873-1884.*
V. Haridas et al., "Gelatin and topochemical polymerization of peptide dendrimers," New Journal of Chemistry, 35, published Oct. 18, 2010, pp. 303-309.*
M. Shomon, "How Temperature Can Affect Medication Stability," <https://www.verywellhealth.com/how-temperature-can-affect-medication-stability-3233264?print>, Very Well Health, published Jul. 11, 2020, pp. 1-6.*
P. Baranowski et al., "Ophthalmic Drug Dosage Forms: Characterisation and Research Methods," Review Article, the Scientific World Journal, Hindawi Publishing Corporation, vol. 2014, published Mar. 18, 2014, pp. 1-14.*
Frokjaer et al., Protein Drug Stability: a Formulation Challenge, Nature/Reviews/DrugDiscovery, Apr. 2005, vol. 4, 298-306.
Wang et al., Technical Report No. 10, Parenteral Formulations of Proteins and Peptides: Stability and Stabilizers, Journal of Parenteral Science & Technology, Supplement vol. 42, No. 25, 1988, S3-S26.
Haridas et al., Gelation and topochemical polymerization of peptide dendrimers, New Journal of Chemistry, 2011, 35, 303-309.
Haridas et al., Multi-Tier Dendrimers with an Aromatic Core, European Journal of Organic Chemistry, 10, 2009, 1570-1577.

(Continued)

*Primary Examiner* — Monica A Shin
(74) *Attorney, Agent, or Firm* — RatnerPrestia

(57) ABSTRACT

The present disclosure relates to a formulation including: a) a dendron of Formula I; b) at least one bio-therapeutic; c) at least one buffer; and d) at least one salt, wherein the bio-therapeutic to dendron molar ratio is in the range of 1:0.5-1:3. The dendron stabilizes the bio-therapeutic in the formulation at a temperature of up to 55° C.

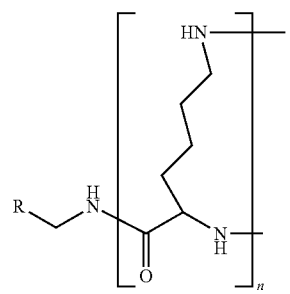

Formula I

11 Claims, 11 Drawing Sheets

(56) References Cited

OTHER PUBLICATIONS

Wang, Instability, stabilization, and formulation of liquid protein pharmaceuticals, International Journal of Pharmaceutics 185 (1999) 129-188.
Haridas et al., Designer peptide dendrimers using click reaction, Tetrahedron 67 (2011) 1873-1884.
International Search Report issued in PCT/IN2017/050233, dated Aug. 24, 2017, 2 pages.
Written Opinion of the International Searching Authority issued in PCT/IN2017/050233, dated Aug. 24, 2017, 5 pages.
Dubey, P., et al., "Dendrons and dendrimers as pseudochaperonins for refolding of proteins", RSC Advances, vol. 3(21), Jan. 1, 2013, pp. 8016-8020, XP055746055.
Supplementary European Search Report for European Application No. 17 874 795.2, dated Nov. 19, 2020, 7 pages.

\* cited by examiner

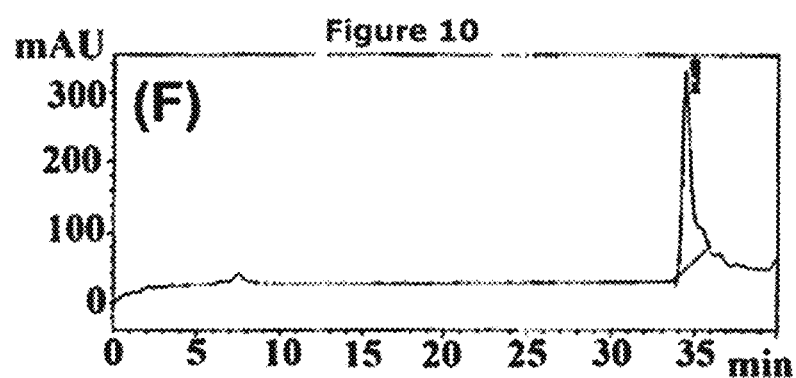

FORMULATION FOR STABILIZING BIO-THERAPEUTICS

CROSS REFERENCE TO RELATED APPLICATIONS

This application is the U.S. National Phase Application of PCT/IN2017/050233, filed Jun. 8, 2017, which claims priority to Indian Patent Application No. 201611040627, filed Nov. 28, 2016, the contents of such applications being incorporated by reference herein.

TECHNICAL FIELD OF THE INVENTION

The present disclosure relates to a formulation for stabilizing bio-therapeutics. The present disclosure also relates to a process for the preparation of the formulation.

The present disclosure further relates to a dendron, which is an important component of the formulation, and a process for the preparation of the dendron.

The present disclosure further relates to a formulation for stabilizing bio-therapeutics, which can be used for curative purposes.

BACKGROUND OF THE INVENTION

'Bio-therapeutics', broadly, is a field of study that covers therapeutic materials produced using biological means, including recombinant DNA technology. The term 'bio-therapeutics', in another sense, also refers to the aforesaid materials or products which exhibit therapeutic activity. Bio-therapeutics include, but are not limited to, classes of compounds such as monoclonal antibodies, cytokines, growth factors, hormones, interferons, interleukins, anticoagulants, bone morphogenetic proteins, antigens, and enzymes. Monoclonal antibodies are antibodies that are made by identical immune cells that are all clones of a unique parent cell. Monoclonal antibodies find wide applications in immunohistochemistry which deals with the detection of antigens in cells of a tissue section, based on the principle of antibodies binding specifically to antigens in tissues. They also find applications in immunofluorescence test which allows the visualization of location of target molecules through the cell. Cytokines which are produced by a variety of cells including immune cells like macrophages, B lymphocytes, etc., play an important role in cell signaling. Growth factors, of which hormones is a subclass, stimulate cellular growth, proliferation, cellular differentiation, and healing.

Interferons are a type of cytokines, which are released by host cells in response to pathogens such as viruses, bacteria, and parasites. They are so named because of their ability to create interference in viral replication by shielding cells from virus infections. Interleukins, alike interferons, are a subclass of the larger group of cytokines. They are an important part of the immune system, and a deficiency of some interleukins is known to be responsible for some of the autoimmune diseases and immune deficiency in general. Anticoagulants, as the name suggests, are compounds that prevent blood clotting (coagulation). An example of this class, autoprothrombin IIA, plays an important role in regulating anticoagulation and preserving the perviousness of blood vessel walls in humans and other animals.

Bone morphogenetic proteins (BMPs) are also considered to be one of the important growth factors and are of significance because of their role in bone and cartilage formation. BMPs have been known to coordinate vital morphogenetic or growth signals. Cancer and related ailments generally involve a disturbance in regulation of the BMP signaling system. Antigens, though generally defined as toxins or foreign bodies eliciting immune response, can sometimes also be a part of host itself. Antigens, as bio-therapeutics, find application in the enzyme-linked immunosorbent assay (ELISA), which is diagnostic tool, based on the principle of specific antigen-antibody interaction. Additionally, they have also found utility in conjugate vaccines wherein a poor antigen is covalently attached to a strong antigen thereby triggering a strong immunological response.

Enzymes are another class of bio-therapeutics and have a plethora of biological and chemical applications. Besides catalyzing biochemical reactions, they also find applications as catalysts in synthetic chemistry. From a bio-therapeutic perspective they assume even higher significance. An especially important application of enzymes has been Directed Enzyme Prodrug Therapy (DEPT) which constitutes an important anti-cancer treatment. With help of DEPT, enzymes are introduced into body, which transform prodrugs with poor biological activity to their active forms at the targeted site. Many of the available chemotherapy drugs have been proven inefficient for the want of tumor specificity. Thus, the dosage levels required to exhibit therapeutic effect often prove toxic to other tissues. DEPT lowers the overall toxicity of the drug by attaining high levels of active drug exclusively at the targeted site.

The description in preceding paragraphs defines bio-therapeutics according to the biological functions they perform and the applications they find. When defined in terms of their molecular structures though, most of them are proteins, with varying degrees of structural complexity. Proteins are large biomolecules consisting of one or more long chains of amino acid residues. Proteins contain at least one, long polypeptide unit, which is a linear chain of amino acid residues. In general short polypeptides are not considered proteins. The boundary in terms of chain length or molecular size, that demarcates polypeptides and proteins, though, is not conclusively clear.

Three dimensional structures of proteins are of paramount importance, because there is a strong correlation between the three dimensional structure of a protein and the activity it exhibits. Proteins arrange themselves into various spatial conformations, a phenomenon commonly referred to as 'folding'. The way a certain protein folds is governed by a number of non-covalent interactions; the most important of them being hydrogen bonding. Other such non-covalent interactions include ionic interactions, Van der Waals forces, and hydrophobic packing. The aforementioned structure-activity correlation necessitates that the protein be held in a specific spatial conformation to display the desired activity. Protein degradation can occur in many ways depending upon conditions the protein is subjected to. One way protein degradation occurs is protein denaturation. Protein denaturation which is defined as disruption of tertiary and secondary structure of protein leads to unfolding of proteins from their characteristic alpha helix and beta sheet structures to more random shapes. Denatured proteins exhibit, inter alia, characteristics like conformational changes and aggregation. However, the most important effect of denaturation of proteins is the loss of desired activity that it exhibits in its native state.

There are many ways in which protein denaturation can occur. Chemically, it can occur by interaction of the protein with acids, bases, solvents, cross-linking reagents, and chaotropic agents. Most chemically induced denaturation occurs by disruption of hydrogen bonding in the protein in its native state. Denaturation can also be induced by mechanical agitation or heat. Heat supplies kinetic energy to the molecules and beyond a certain point this energy is sufficient to overcome hydrogen bonding, thereby causing denaturation. In addition to denaturation, there are other ways too, in which protein degradation can occur. These include degradation by aggregation and precipitation.

Research has been carried out in the past with objective of stabilizing proteins to avoid denaturation. WO1990003784 describes formulations comprising cyclodextrin-protein complexes for stabilizing the protein.

U.S. Pat. No. 5,730,969 also discloses a cyclodextrin derivative to stabilize proteins and prevent denaturation and aggregation.

U.S. Pat. No. 4,457,916 discloses a method for stabilizing Tumor Necrosis Factor (TNF) by adding a non-ionic surfactant as a stabilizing agent.

Non-patent literature has also been published describing use of various excipients like salts, sugars, amino acids, surfactants, and polymers etc.[1,2]

A concise description of the factors affecting stability of proteins and stabilizers that can be used has also been published.[3] This report details various ways by which degradation of a protein comes about and provides remedies to mitigate the same by use of various excipients, thereby stabilizing the parenteral formulations of proteins. The excipients used include serum albumin, fatty acids, amino acids, phospholipids, metals, surfactants, reducing agents, metal chelating agents, polyols, polyvinylpyrrolidone, hydrolyzed gelatin and ammonium sulfate. It also discusses use of cryoprotectants such as carbohydrates, alcohols, and glutamic acid, which reduce degradation happening at low temperatures.

Most of the aforementioned work however, discloses methods to stabilize proteins using various excipients, which still require preservation of the proteins at low temperatures. In other words, although these methods confer chemical stability, they do not address the problem of thermal degradation. This poses a significant problem, as storing proteins at a lower temperature creates energy requirements, thereby increasing the costs involved. The problem becomes graver for the densely populated parts of the developing world. High population implies higher requirement of biotherapeutics, which in turn implies a requirement for large scale refrigeration. The costs involved thereby can make it impracticable and prohibitive for the smaller economies. The severity of this problem is especially higher in Sub-Saharan African region which is already grappling with huge demand-supply gap in terms of life-saving drugs and where temperatures regularly soar beyond 45° C. This means that whatever little stock of life-saving drugs such regions manage to garner is at the peril of being rendered inactive. In view of all the aforementioned problems, it is a desperate need of the hour to devise mechanisms to conserve proteins at higher temperatures, if we are to avert a major global health crisis.

REFERENCES

1) Frokjaer, S., & Otzen, D. E. (2005). Protein drug stability: a formulation challenge. *Nature Reviews Drug Discovery*, 4, 298-306.
2) Wang, W. (1999). Instability, stabilization, and formulation of liquid protein pharmaceuticals. *International journal of pharmaceutics*, 185, 129-188.
3) Wang et al, Journal of Parenteral Science and Technology, Technical Report No. 10, "Parenteral Formulations of Proteins and Peptides: Stability and Stabilizers", Supplement Volume 42, Number 25, 1988, pp. S3-S26.
4) Haridas, V., Sharma, Y. K., & Naik, S. (2009). Multi-Tier Dendrimer with an Aromatic Core. *European Journal of Organic Chemistry*, 10, 1570-1577.
5) Haridas, V., Sharma, Y. K., Creasey, R., Sahu, S., Gibson, C. T., & Voelcker, N. H. (2011). Gelation and topochemical polymerization of peptide dendrimers. *New Journal of Chemistry*, 35, 303-309.
6) Haridas, V., Sharma, Y. K., Sahu, S., Verma, R. P., Sadanandan, S., Kacheshwar, B. G. (2011). Designer peptide dendrimers using click reaction. *Tetrahedron*, 67, 1873-1884.

SUMMARY OF THE INVENTION

The present disclosure relates to a formulation comprising:

a) a dendron of Formula I,

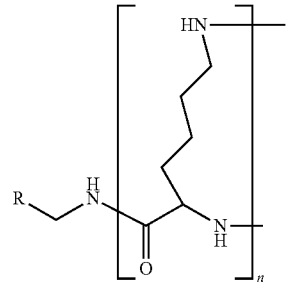

Formula I wherein R is selected from the group consisting of hydrogen, halogen, $C_{1-16}$ alkyl, $C_{5-22}$ aryl, $C_{1-16}$ alkoxy, $C_{1-16}$ haloalkyl, $C_{3-12}$ cycloalkyl, $C_{1-20}$ heteroaryl, $C_{1-20}$ heterocyclyl, $C_{2-16}$ alkenyl, $C_{2-16}$ alkynyl, —COOR$_a$, —C(O)R$_b$, —C(O)NR$_b$R$_c$, —NR$_d$R$_e$, —NR$_b$C(O)R$_c$, —OC(O)R$_b$, wherein R$_a$ is selected from the group consisting of hydrogen, $C_{1-16}$ alkyl, $C_{5-22}$ aryl, $C_{3-12}$ cycloalkyl, $C_{1-20}$ heteroaryl, $C_{1-20}$ heterocyclyl; R$_b$ and R$_c$ are independently selected from the group consisting of hydrogen, $C_{1-16}$ alkyl, $C_{5-22}$ aryl, $C_{1-16}$ haloalkyl, $C_{3-12}$ cycloalkyl, $C_{1-20}$ heteroaryl, $C_{1-20}$ heterocyclyl; R$_d$ and R$_e$ are independently selected from the group consisting of hydrogen, $C_{1-16}$ alkyl, $C_{5-22}$ aryl, $C_{1-16}$ haloalkyl, $C_{3-12}$ cycloalkyl, $C_{1-20}$ heteroaryl, $C_{1-20}$ heterocyclyl, wherein 'n' is in the range of 1-15; the branch growth follows a dendritic pattern; all

groups of all repeating units are attached to another repeating unit till the penultimate repeating unit of every branch, and the

groups of the terminal repeating units of all branches are attached to an atom or a functional group independently selected from the group consisting of hydrogen, tert-butyloxycarbonyl (Boc), and fluorenylmethyloxycarbonyl (Fmoc);
a) at least one bio-therapeutic;
b) at least one buffer solution; and
c) at least one salt,
wherein the bio-therapeutic to dendron molar ratio is in the range of 1:0.5-1:3 and the dendron stabilizes the bio-therapeutic in the formulation at a temperature of up to 55° C.

The present disclosure further relates to a process for preparing a formulation comprising:
a) a dendron of Formula I,

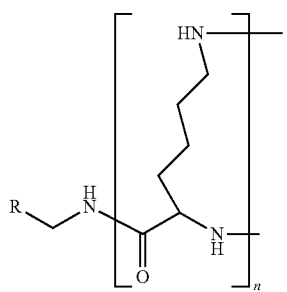

Formula I wherein R is selected from the group consisting of hydrogen, halogen, $C_{1-16}$ alkyl, $C_{5-22}$ aryl, $C_{1-16}$ alkoxy, $C_{1-16}$ haloalkyl, $C_{3-12}$ cycloalkyl, $C_{1-20}$ heteroaryl, $C_{1-20}$ heterocyclyl, $C_{2-16}$ alkenyl, $C_{2-16}$ alkynyl, —COOR$_a$, —C(O)R$_b$, —C(O)NR$_b$R$_c$, —NR$_d$R$_e$, —NR$_b$C(O)R$_c$, —OC(O)R$_b$, wherein R$_a$ is selected from the group consisting of hydrogen, $C_{1-16}$ alkyl, $C_{5-22}$ aryl, $C_{3-12}$ cycloalkyl, $C_{1-20}$ heteroaryl, $C_{1-20}$ heterocyclyl; R$_b$ and R$_c$ are independently selected from the group consisting of hydrogen, $C_{1-16}$ alkyl, $C_{5-22}$ aryl, $C_{1-16}$ haloalkyl, $C_{3-12}$ cycloalkyl, $C_{1-20}$ heteroaryl, $C_{1-20}$ heterocyclyl; R$_d$ and R$_e$ are independently selected from the group consisting of hydrogen, $C_{1-16}$ alkyl, $C_{5-22}$ aryl, $C_{1-16}$ haloalkyl, $C_{3-12}$ cycloalkyl, $C_{1-20}$ heteroaryl, $C_{1-20}$ heterocyclyl, wherein 'n' is in the range of 1-15; the branch growth follows a dendritic pattern; all

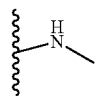 [SMILES: *NC]

groups of all repeating units are attached to another repeating unit till the penultimate repeating unit of every branch, and the

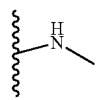

groups of the terminal repeating units of all branches are attached to an atom or a functional group independently selected from the group consisting of hydrogen, tert-butyloxycarbonyl (Boc), and fluorenylmethyloxycarbonyl (Fmoc);
b) at least one bio-therapeutic;
c) at least one buffer solution; and
d) at least one salt,
wherein the bio-therapeutic to dendron molar ratio is in the range of 1:0.5-1:3 and the dendron stabilizes the bio-therapeutic in the formulation at a temperature of up to 55° C.; the process comprising the steps of: (a) contacting at least one buffer solution and at least one salt solution with at least one bio-therapeutic to obtain a mixture; (b) contacting the mixture from step (a) with the dendron to obtain the formulation.

The present disclosure further relates to a formulation, wherein the bio-therapeutics remain stable at high temperatures of up to 55° C. without considerable degradation, and can be used for curative purposes.

These and other features, aspects, and advantages of the present subject matter will become better understood with reference to the following description. This summary is provided to introduce a selection of concepts in a simplified form. This summary is not intended to identify key features or essential features of the disclosure, nor is it intended to be used to limit the scope of the subject matter.

BRIEF DESCRIPTION OF DRAWINGS

The detailed description is described with reference to the accompanying figures. In the figures, the left-most digit(s) of a reference number identifies the figure in which the reference number first appears. The same numbers are used throughout the drawings to reference like features and components.

FIGS. 2A, 2B, 2C, and 2D represent graphs depicting percentage of monomer loss for formulations with PS 80, dendron A2, dendron B2, and dendron C2 respectively.

FIGS. 3A, 3B, 3C, and 3D represent graphs depicting percentage of aggregates for formulations with PS 80, dendron A2, dendron B2, and dendron C2 respectively.

FIGS. 4A, 4B, 4C, and 4D represent graphs depicting percentage of fragments for formulations with PS 80, dendron A2, dendron B2, and dendron C2 respectively.

DETAILED DESCRIPTION OF THE INVENTION

Figure 1:
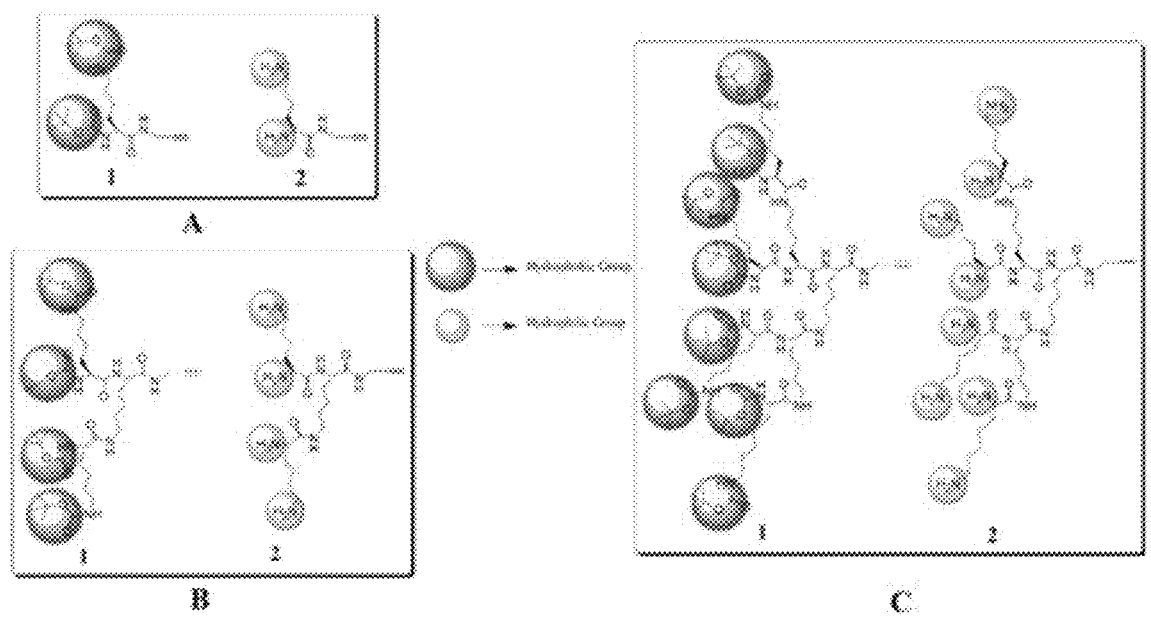
FIGS. 1A-C depicts various lysine based dendrons synthesized to be used in the formulations for stabilizing the proteins. The various lysine based dendrons that FIG. 1 depicts are as follows: lysine-based dendrons of first generation (A1, A2); second generation (B1, B2); third generation (C1, C2).

Those skilled in the art will be aware that the present disclosure is subject to variations and modifications other than those specifically described. It is to be understood that the present disclosure includes all such variations and modifications. The disclosure also includes all such steps, features, compositions and compounds referred to or indicated in this specification, individually or collectively, and any and all combinations of any or more of such steps or features.

Definitions

For convenience, before further description of the present disclosure, certain terms employed in the specification, and examples are collected here. These definitions should be read in the light of the remainder of the disclosure and understood as by a person of skill in the art. The terms used herein have the meanings recognized and known to those of skill in the art, however, for convenience and completeness, particular terms and their meanings are set forth below.

The articles "a", "an" and "the" are used to refer to one or to more than one (i.e., to at least one) of the grammatical object of the article.

The terms "comprise" and "comprising" are used in the inclusive, open sense, meaning that additional elements may be included. Throughout this specification, unless the context requires otherwise the word "comprise", and variations, such as "comprises" and "comprising", will be understood to imply the inclusion of a stated element or step or group of element or steps but not the exclusion of any other element or step or group of element or steps.

The term "including" is used to mean "including but not limited to". "Including" and "including but not limited to" are used interchangeably.

The term "dendron" refers to a repetitively branched molecule. The repeating unit of the dendron of the present invention is the amino acid residue lysine.

The term "monoclonal antibodies" refers to antibodies that are made by identical immune cells that are all clones of a unique parent cell. Monoclonal antibodies include IgE monoclonal antibodies, IgG1 monoclonal antibodies, peroxidase-anti-peroxidase conjugated monoclonal antibodies, human chorionic gonadotropin monoclonal antibodies, and anti-rabies monoclonal antibodies.

The term "cytokines" refers to a substance produced by a variety of cells including immune cells like macrophages, B lymphocytes, etc., which play an important role in cell signaling. Cytokines include chemokines, lymphokines, and tumor necrosis factors.

The term "growth factors" refers to a substance, which is required for the stimulation of growth in living cells. Growth factors include hormones.

The term "interferons" refers to type of cytokines, which are released by host cells in response to pathogens such as viruses, bacteria, and parasites. Interferons include type I, type II, and type III interferons.

The term "interferons" refers to a group of cytokines that play an important part in the immune system. Interleukins include interleukins IL-1 to IL-17.

The term "anticoagulants" refers to compounds that prevent blood clotting (coagulation). Anticoagulants include autoprothrombin IIA.

The term "bone morphogenetic proteins" refers to one of the important growth factors which play a critical role in bone and cartilage formation. Bone morphogenetic proteins include bone morphogenetic proteins BMP-1 to BMP-15.

The term "antigens" refers to toxins or foreign bodies eliciting immune response, though they can sometimes also be a part of host itself.

The term "enzyme" refers to a substance produced by a living organism which acts as a catalyst to bring about a certain biochemical reaction. Enzymes include lipases, amylases, maltases, pepsins, proteases.

The terms, monoclonal antibodies, cytokines, growth factors, hormones, interferons, interleukins, anticoagulants, bone morphogenetic proteins, antigens, and enzymes can be proteins or non-proteins, though majority of them are generally proteins. The ones contemplated by the present invention are the ones with protein structures.

The term "anti-bacterial agent" refers to any substance that protects the protein from bacterial contamination. Antibacterial agents include, but are not limited to, sodium azide, thymol, benzalkonium chloride, and glycerol.

In the structural formulae given herein and throughout the present disclosure, the following terms have the indicated meaning, unless specifically stated otherwise.

The term "alkyl" refers to a monoradical branched or unbranched saturated hydrocarbon chain having from 1 to 16 carbon atoms. This term is exemplified by groups such as methyl, ethyl, n-propyl, iso-propyl, n-butyl, iso-butyl, t-butyl, n-hexyl, n-decyl, tetradecyl, and the like. By way of further example, a $C_1$-$C_{16}$ alkyl contains at least one but no more than 16 carbon atoms. A methyl group (i.e., $CH_3$—) is an example of a $C_1$ alkyl radical. A dodecyl group (i.e., $CH_3(CH_2)_{11}$—) is an example of a $C_{12}$ alkyl radical. The groups may be optionally substituted.

The term "alkenyl" refers to a branched or unbranched hydrocarbon chain having from 2 to 16 carbon atoms, and having at least one carbon-carbon double bond. This term is exemplified by groups such as ethenyl, n-propenyl, n-butenyl, n-hexenyl, and the like. The groups may be optionally substituted.

The term "alkynyl" refers to a branched or unbranched hydrocarbon chain having from 2 to 16 carbon atoms, and having at least one carbon-carbon triple bond. This term is exemplified by groups such as ethynyl, n-propynyl, n-butynyl, n-hexynyl, and the like. The groups may be optionally substituted.

It will be understood that "substitution" or "substituted with" includes the implicit proviso that such substitution is in accordance with permitted valence of the substituted atom and the substituent, and that the substitution results in a stable compound, e.g., which does not spontaneously undergo transformation such as by rearrangement, cyclization, elimination, etc.

As used herein, the term "substituted" is contemplated to include all permissible substituents of organic compounds. In a broad aspect, the permissible substituents include acyclic and cyclic, branched and unbranched, carbocyclic and heterocyclic, aromatic and nonaromatic substituents of organic compounds. Illustrative substituents include, for example, those described herein. The permissible substituents can be one or more and the same or different for appropriate organic compounds. For purposes of this invention, the heteroatoms such as nitrogen may have hydrogen substituents and/or any permissible substituents of organic compounds described herein which satisfy the valences of the heteroatoms.

"Halo" or "Halogen", alone or in combination with any other term means halogens such as chloro (Cl), fluoro (F), bromo (Br) and iodo (I).

The term "aryl" refers to an aromatic carbocyclic group of 5 to 22 carbon atoms having a single ring or multiple rings, or multiple condensed (fused) rings.

The term "alkoxy" refers to an alkyl group of 1 to 16 carbon atoms attached via an oxygen linkage to the rest of the molecule, which may be optionally substituted by one or more substituents. Preferred alkoxy groups, without limitation, include —OCH$_3$, —OC$_2$H$_5$ and the like.

The term "cycloalkyl" refers to non-aromatic mono or polycyclic ring system of about 3 to 12 carbon atoms, which may be optionally substituted by one or more substituent's. The polycyclic ring denotes hydrocarbon systems containing two or more ring systems with one or more ring carbon atoms in common, i.e., a Spiro, fused or bridged structures. Preferred cycloalkyl groups include, without limitation, cyclopropyl, cyclobutyl, cyclopentyl, cyclohexyl, cyclooctanyl, perhydronaphthyl, adamantyl, noradamantyl and norbornyl groups, bridged cyclic groups or spirobicyclic groups e.g. Spiro [4.4] non-2-yl and the like.

The term "heteroaryl" refers to a heteroaromatic carbocyclic group of 1 to 20 carbon atoms with one to five heteroatoms selected from nitrogen, phosphorus, oxygen and sulfur, having a single ring (e.g. pyridine) or multiple rings (e.g. isoquinoline), or multiple condensed (fused) rings. Preferred heteroaryls include thiophene, pyrazole, thiazole, pyridine, and the like. The groups may be optionally substituted.

The term "heterocyclyl" refers to a stable 1 to 20 membered ring radical, which consists of carbon atoms and from one to five heteroatoms selected from nitrogen, phosphorus, oxygen and sulfur. For purposes of this invention the heterocyclic ring radical may be monocyclic, bicyclic or tricyclic ring systems, and the nitrogen, phosphorus, carbon, oxygen or sulfur atoms in the heterocyclic ring radical may be optionally oxidized to various oxidation states. In addition, the nitrogen atom may be optionally quaternized; and the ring radical may be partially or fully saturated. Preferred heterocyclyl groups, without limitation, include azetidinyl, acridinyl, benzodioxolyl, benzodioxanyl, benzofuranyl, carbazolyl, cinnolinyl, dioxolanyl, indolizinyl, naphthyridinyl, perhydroazepinyl, phenazinyl, phenothiazinyl, phenoxazinyl, phthalazinyl, pyrazolyl, pyridyl, pteridinyl, purinyl, quinazolinyl, quinoxalinyl, quinolinyl, isoquinolinyl, tetrazolyl, imidazolyl, tetrahydroisoquinolinyl, piperidinyl, piperazinyl, homopiperazinyl, 2-oxoazepinyl, azepinyl, pyrrolyl, 4-piperidonyl, pyrrolidinyl, pyrazinyl, pyrimidinyl, pyridazinyl, oxazolyl, oxazolidinyl, triazolyl, indanyl, isoxazolyl, isoxazolidinyl, thiazolyl, thiazolinyl, thiazolidinyl, isothiazolyl, quinuclidinyl, isothiazolidinyl, indolyl, isoindolyl, indolinyl, isoindolinyl, octahydroindolyl, octahydroisoindolyl, quinolyl, isoquinolyl, decahydroisoquinolyl, benzimidazolyl, thiadiazolyl, benzopyranyl, benzothiazolyl, benzooxazolyl, thienyl, morpholinyl, thiomorpholinyl, thiamorpholinyl sulfoxide, furyl, tetrahydrofuryl, tetrahydropyranyl, chromanyl and isochromanyl.

The term "alkenyl" refers to hydrocarbon group containing 2-16 carbon atoms and containing at least one carbon-carbon double bond. Preferred alkenyl groups, without limitation, include ethenyl, propenyl, butenyl, and the like. The groups may be optionally substituted.

The term "alkynyl" refers to hydrocarbon group containing 2-16 carbon atoms and containing at least one carbon-carbon triple bond. Preferred alkynyl groups, without limitation, include ethynyl, propynyl, butynyl, and the like. The groups may be optionally substituted.

The compounds described herein may contain one or more chiral centers and/or double bonds and therefore, may exist as stereoisomers, such as double-bond isomers (i.e., geometric isomers), regioisomers, enantiomers or diastereomers. Accordingly, the chemical structures depicted herein encompass all possible enantiomers and stereoisomers of the illustrated or identified compounds including the stereoisomerically pure form (e.g., geometrically pure, enantiomerically pure or diastereomerically pure) and enantiomeric and stereoisomeric mixtures. Enantiomeric and stereoisomeric mixtures can be resolved into their component enantiomers or stereoisomers using separation techniques or chiral synthesis techniques well known to the person skilled in the art. The compounds may also exist in several tautomeric forms including the enol form, the keto form and mixtures thereof. Accordingly, the chemical structures depicted herein encompass all possible tautomeric forms of the illustrated or identified compounds. It is also understood that some isomeric form such as diastereomers, enantiomers and geometrical isomers can be separated by physical and/or chemical methods and by those skilled in the art. Pharmaceutically acceptable solvates may be hydrates or comprising of other solvents of crystallization such as alcohols, ether, and the like.

As discussed above, preserving proteins at a higher temperature without thermal degradation is a much sought-after goal, given the value it will add to the global effort being made towards mitigating life-threatening diseases. The present disclosure provides a dendron-based formulation to stabilize proteins at higher temperatures.

According to one embodiment, the present disclosure relates to a formulation comprising:
a) a dendron of Formula I,

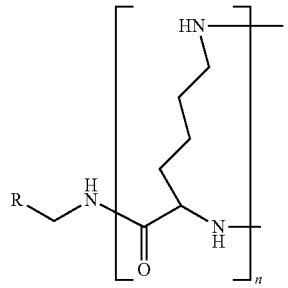

Formula I wherein R is selected from the group consisting of hydrogen, halogen, $C_{1-16}$ alkyl, $C_{5-22}$ aryl, $C_{1-16}$ alkoxy, $C_{1-16}$ haloalkyl, $C_{3-12}$ cycloalkyl, $C_{1-20}$ heteroaryl, $C_{1-20}$ heterocyclyl, $C_{2-16}$ alkenyl, $C_{2-16}$ alkynyl, —COOR$_a$, —C(O)R$_b$, —C(O)NR$_b$R$_c$, —NR$_d$R$_e$, —NR$_b$C(O)R$_c$, —OC(O)R$_b$, wherein R$_a$ is selected from the group consisting of hydrogen, $C_{1-16}$ alkyl, $C_{5-22}$ aryl, $C_{3-12}$ cycloalkyl, $C_{1-20}$ heteroaryl, $C_{1-20}$ heterocyclyl; R$_b$ and R$_c$ are independently selected from the group consisting of hydrogen, $C_{1-16}$ alkyl, $C_{5-22}$ aryl, $C_{1-16}$ haloalkyl, $C_{3-12}$ cycloalkyl, $C_{1-20}$ heteroaryl, $C_{1-20}$ heterocyclyl; R$_d$ and R$_e$ are independently selected from the group consisting of hydrogen, $C_{1-16}$ alkyl, $C_{5-22}$ aryl, $C_{1-16}$ haloalkyl, $C_{3-12}$ cycloalkyl, $C_{1-20}$ heteroaryl, $C_{1-20}$ heterocyclyl, wherein 'n' is in the range of 1-15; the branch growth follows a dendritic pattern; all

groups of all repeating units are attached to another repeating unit till the penultimate repeating unit of every branch, and the

groups of the terminal repeating units of all branches are attached to an atom or a functional group independently selected from the group consisting of hydrogen, tert-butyloxycarbonyl (Boc), and fluorenylmethyloxycarbonyl (Fmoc);
b) at least one bio-therapeutic;
c) at least one buffer solution; and
d) at least one salt,
wherein the bio-therapeutic to dendron molar ratio is in the range of 1:0.5-1:3 and the dendron stabilizes the bio-therapeutic in the formulation at a temperature of up to 55° C.

According to one embodiment, the present disclosure relates to a formulation as described herein, wherein the bio-therapeutic is selected from the group consisting of monoclonal antibodies, cytokines, growth factors, hormones, interferons, interleukins, anticoagulants, bone morphogenetic proteins, antigens, and enzymes.

According to one embodiment, the present disclosure relates to a formulation as described herein, wherein the monoclonal antibody is IgG1 monoclonal antibody.

According to one embodiment, the present disclosure relates to a formulation as described herein, wherein the buffer solution is selected from the group consisting of phosphate buffer, citrate buffer, acetate buffer, histidine buffer, succinate buffer, and glycine buffer.

According to another embodiment, the present disclosure relates to a formulation as described herein, wherein the salt is selected from the group consisting of sodium chloride, potassium chloride, calcium chloride, potassium iodide, magnesium chloride, magnesium sulfate, sodium citrate, and sodium acetate.

According to yet another embodiment, the present disclosure relates to a formulation comprising:
a) a dendron of Formula I,

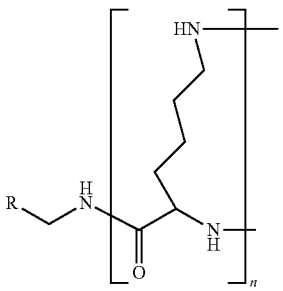

Formula I wherein R is selected from the group consisting of hydrogen, halogen, $C_{1-10}$ alkyl, $C_{5-22}$ aryl, $C_{1-10}$ alkoxy, $C_{1-10}$ haloalkyl, $C_{3-12}$ cycloalkyl, $C_{1-20}$ heteroaryl, $C_{1-20}$ heterocyclyl, $C_{2-16}$ alkenyl, $C_{2-16}$ alkynyl, —COOR$_a$, —C(O)R$_b$, —C(O)NR$_b$R$_c$, —NR$_d$R$_e$, —NR$_b$C(O)R$_c$, —OC(O)R$_b$, wherein R$_a$ is selected from the group consisting of hydrogen, $C_{1-16}$ alkyl, $C_{5-22}$ aryl, $C_{3-12}$ cycloalkyl, $C_{1-20}$ heteroaryl, $C_{1-20}$ heterocyclyl; R$_b$ and R$_c$ are independently selected from the group consisting of hydrogen, $C_{1-16}$ alkyl, $C_{5-22}$ aryl, $C_{1-16}$ haloalkyl, $C_{3-12}$ cycloalkyl, $C_{1-20}$ heteroaryl, $C_{1-20}$ heterocyclyl; R$_d$ and R$_e$ are independently selected from the group consisting of hydrogen, $C_{1-16}$ alkyl, $C_{5-22}$ aryl, $C_{1-16}$ haloalkyl, $C_{3-12}$ cycloalkyl, $C_{1-20}$ heteroaryl, $C_{1-20}$ heterocyclyl, wherein 'n' is in the range of 1-15; the branch growth follows a dendritic pattern; all

groups of all repeating units are attached to another repeating unit till the penultimate repeating unit of every branch, and the

groups of the terminal repeating units of all branches are attached to an atom or a functional group independently selected from the group consisting of hydrogen, tert-butyloxycarbonyl (Boc), and fluorenylmethyloxycarbonyl (Fmoc);
b) at least one monoclonal antibody;
c) at least one buffer solution; and
d) sodium chloride,
wherein the monoclonal antibody to dendron molar ratio is in the range of 1:0.5-1:3 and the dendron stabilizes the monoclonal antibody in the formulation at a temperature of up to 55° C.

According to yet another embodiment, the present disclosure relates to a formulation comprising:

a) a dendron of Formula I,

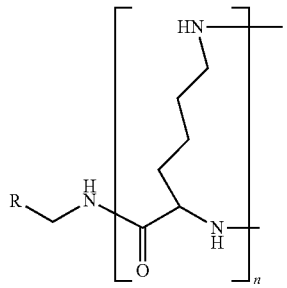

Formula I wherein R is selected from the group consisting of hydrogen, halogen, $C_{1-16}$ alkyl, $C_{5-22}$ aryl, $C_{1-16}$ alkoxy, $C_{1-16}$ haloalkyl, $C_{3-12}$ cycloalkyl, $C_{1-20}$ heteroaryl, $C_{1-20}$ heterocyclyl, $C_{2-16}$ alkenyl, $C_{2-16}$ alkynyl, —COOR$_a$, —C(O)R$_b$, —C(O)NR$_b$R$_c$, —NR$_d$R$_e$, —NR$_b$C(O)R$_c$, —OC(O)R$_b$, wherein R$_a$ is selected from the group consisting of $C_{1-16}$ straight chain aliphatic group, $C_{5-22}$ aryl, $C_{3-12}$ cycloalkyl, $C_{1-20}$ heteroaryl, $C_{1-20}$ heterocyclyl; R$_b$ and R$_c$ are independently selected from the group consisting of hydrogen, $C_{1-16}$ alkyl, $C_{5-22}$ aryl, $C_{1-16}$ haloalkyl, $C_{3-12}$ cycloalkyl, $C_{1-20}$ heteroaryl, $C_{1-20}$ heterocyclyl; R$_d$ and R$_e$ are independently selected from the group consisting of $C_{1-16}$ alkyl, $C_{5-22}$ aryl, $C_{1-16}$ haloalkyl, $C_{3-12}$ cycloalkyl, $C_{1-20}$ heteroaryl, $C_{1-20}$ heterocyclyl, wherein 'n' is in the range of 1-15; the branch growth follows a dendritic pattern; all

groups of all repeating units are attached to another repeating unit till the penultimate repeating unit of every branch, and the

groups of the terminal repeating units of all branches are attached to an atom or a functional group independently selected from the group consisting of hydrogen, tert-butyloxycarbonyl (Boc), and fluorenylmethyloxycarbonyl (Fmoc);

b) at least one bio-therapeutic;

c) at least one buffer solution; and d) at least one salt, wherein the bio-therapeutic to dendron molar ratio is in the range of 1:0.5-1:3 and the dendron stabilizes the bio-therapeutic in the formulation at a temperature of up to 55° C.

According to yet another embodiment, the present disclosure relates to a formulation comprising:

a) a dendron of Formula I,

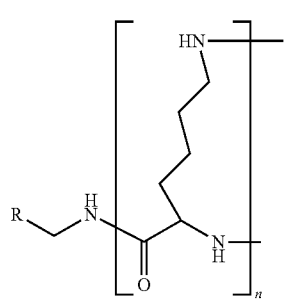

Formula I wherein R is selected from the group consisting of hydrogen, $C_{1-16}$ alkyl, $C_{5-22}$ aryl, $C_{1-16}$ alkoxy, $C_{3-12}$ cycloalkyl, $C_{1-20}$ heteroaryl, $C_{1-20}$ heterocyclyl, $C_{2-16}$ alkenyl, $C_{2-16}$ alkynyl, —COOR$_a$, —C(O)R$_b$, —C(O)NR$_b$R$_c$, —NR$_b$C(O)R$_c$, —OC(O)R$_b$, wherein R$_a$ is selected from the group consisting of $C_{1-16}$ straight chain aliphatic group, $C_{5-22}$ aryl, $C_{3-12}$ cycloalkyl, $C_{1-20}$ heteroaryl, $C_{1-20}$ heterocyclyl; R$_b$ and R$_c$ are independently selected from the group consisting of hydrogen, $C_{1-16}$ alkyl, $C_{5-22}$ aryl, $C_{1-16}$ haloalkyl, $C_{3-12}$ cycloalkyl, $C_{1-20}$ heteroaryl, $C_{1-20}$ heterocyclyl, wherein 'n' is in the range of 1-15; the branch growth follows a dendritic pattern; all

groups of all repeating units are attached to another repeating unit till the penultimate repeating unit of every branch, and the

groups of the terminal repeating units of all branches are attached to an atom or a functional group independently selected from the group consisting of hydrogen, tert-butyloxycarbonyl (Boc), and fluorenylmethyloxycarbonyl (Fmoc);

b) at least one bio-therapeutic;

c) at least one buffer solution; and d) at least one salt, wherein the bio-therapeutic to dendron molar ratio is in the range of 1:0.5-1:3 and the dendron stabilizes the bio-therapeutic in the formulation at a temperature of up to 55° C.

According to yet another embodiment, the present disclosure relates to a formulation comprising:
a) a dendron of Formula I,

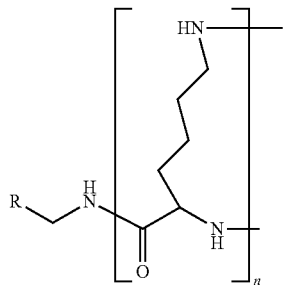

Formula I wherein R is ethynyl,
'n' is in the range of 1-7, the branch growth follows a dendritic pattern; all

groups of all repeating units are attached to another repeating unit till the penultimate repeating unit of every branch, and the

groups of the terminal repeating units of all branches are attached to hydrogen;
b) at least one bio-therapeutic;
c) at least one buffer solution; and
d) at least one salt,
wherein the bio-therapeutic to dendron molar ratio is in the range of 1:0.5-1:3 and the dendron stabilizes the bio-therapeutic in the formulation at a temperature of up to 55° C.

According to one embodiment, the present disclosure relates to a formulation comprising:
a) a dendron of Formula I,

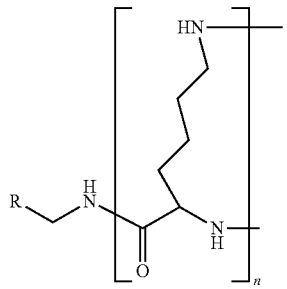

Formula I wherein R is selected from the group consisting of hydrogen, halogen, $C_{1-16}$ alkyl, $C_{5-22}$ aryl, $C_{1-16}$ alkoxy, $C_{1-16}$ haloalkyl, $C_{3-12}$ cycloalkyl, $C_{2-16}$ alkenyl, $C_{2-16}$ alkynyl, —COOR$_a$, —C(O)R$_b$, —C(O)NR$_b$R$_c$, —NR$_d$R$_e$, —NR$_b$C(O)R$_c$, —OC(O)R$_b$, wherein R$_a$ is selected from the group consisting of hydrogen, $C_{1-16}$ alkyl, $C_{5-22}$ aryl, $C_{3-12}$ cycloalkyl, $C_{1-20}$ heteroaryl, $C_{1-20}$ heterocyclyl; R$_b$ and R$_c$ are independently selected from the group consisting of hydrogen, $C_{1-16}$ alkyl, $C_{5-22}$ aryl, $C_{1-16}$ haloalkyl, $C_{3-12}$ cycloalkyl, $C_{1-20}$ heteroaryl, $C_{1-20}$ heterocyclyl; R$_d$ and R$_e$ are independently selected from the group consisting of hydrogen, $C_{1-16}$ alkyl, $C_{5-22}$ aryl, $C_{1-16}$ haloalkyl, $C_{3-12}$ cycloalkyl, $C_{1-20}$ heteroaryl, $C_{1-20}$ heterocyclyl,
wherein 'n' is in the range of 1-15; the branch growth follows a dendritic pattern; all

groups of all repeating units are attached to another repeating unit till the penultimate repeating unit of every branch, and the

groups of the terminal repeating units of all branches are attached to an atom or a functional group independently selected from the group consisting of hydrogen, tert-butyloxycarbonyl (Boc), and fluorenylmethyloxycarbonyl (Fmoc);
b) at least one monoclonal antibody;
c) at least one buffer solution; and
d) sodium chloride,
wherein the monoclonal antibody to dendron molar ratio is in the range of 1:0.5-1:2.5 and the dendron stabilizes the monoclonal antibody in the formulation at a temperature of up to 55° C.

According to one embodiment, the present disclosure relates to a formulation comprising:
a) a dendron of Formula I,

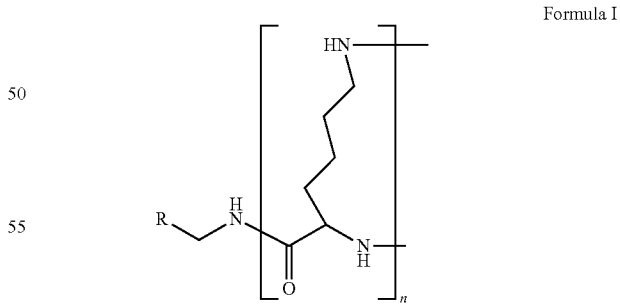

Formula I wherein R is selected from the group consisting of hydrogen, halogen, $C_{1-16}$ alkyl, $C_{5-22}$ aryl, $C_{1-16}$ alkoxy, $C_{1-16}$ haloalkyl, $C_{3-12}$ cycloalkyl, $C_{1-20}$ heteroaryl, $C_{1-20}$ heterocyclyl, $C_{2-16}$ alkenyl, $C_{2-16}$ alkynyl, —COOR$_a$, —C(O)R$_b$, —C(O)NR$_b$R$_c$, —NR$_d$R$_e$, wherein R$_a$ is selected from the group consisting of hydrogen, $C_{1-16}$ alkyl, $C_{5-22}$ aryl, $C_{3-12}$ cycloalkyl, $C_{1-20}$ heteroaryl, $C_{1-20}$ heterocyclyl; R$_b$ and R$_c$ are independently selected from the group consisting of hydrogen, $C_{1-16}$ alkyl, $C_{5-22}$ aryl, $C_{1-16}$ haloalkyl, $C_{3-12}$ cycloalkyl, $C_{1-20}$ heteroaryl, $C_{1-20}$ heterocyclyl; $R_d$ and $R_e$ are independently selected from the group consisting of hydrogen, $C_{1-16}$ alkyl, $C_{5-22}$ aryl, $C_{1-16}$ haloalkyl, $C_{3-12}$ cycloalkyl, $C_{1-20}$ heteroaryl, $C_{1-20}$ heterocyclyl, wherein 'n' is in the range of 1-15; the branch growth follows a dendritic pattern; all

groups of all repeating units are attached to another repeating unit till the penultimate repeating unit of every branch, and the

groups of the terminal repeating units of all branches are attached to an atom or a functional group independently selected from the group consisting of hydrogen, tert-butyloxycarbonyl (Boc), and fluorenylmethyloxycarbonyl (Fmoc);
b) at least one monoclonal antibody;
c) phosphate buffer; and
d) sodium chloride,
wherein the monoclonal antibody to dendron molar ratio is in the range of 1:0.5-1:3 and the dendron stabilizes the monoclonal antibody in the formulation at a temperature of up to 55° C.

According to another embodiment, the present disclosure relates to a formulation comprising:
a) a dendron of Formula I,

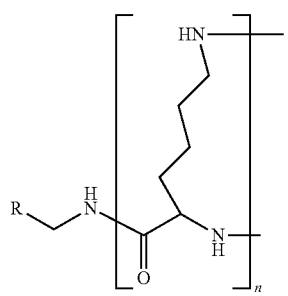

Formula I wherein R is selected from the group consisting of hydrogen, halogen, $C_{1-16}$ alkyl, $C_{5-22}$ aryl, $C_{1-16}$ alkoxy, $C_{1-16}$ haloalkyl, $C_{3-12}$ cycloalkyl, $C_{1-20}$ heteroaryl, $C_{1-20}$ heterocyclyl, $C_{2-16}$ alkenyl, $C_{2-16}$ alkynyl, —COOR$_a$, —C(O)R$_b$, —C(O)N$_R$b$_c$, wherein R$_a$ is selected from the group consisting of hydrogen, $C_{1-16}$ alkyl, $C_{5-22}$ aryl, $C_{3-12}$ cycloalkyl, $C_{1-20}$ heteroaryl, $C_{1-20}$ heterocyclyl; R$_b$ and R$_c$ are independently selected from the group consisting of hydrogen, $C_{1-16}$ alkyl, $C_{5-22}$ aryl, $C_{1-16}$ haloalkyl, $C_{3-12}$ cycloalkyl, $C_{1-20}$ heteroaryl, $C_{1-20}$ heterocyclyl, wherein 'n' is in the range of 1-15; the branch growth follows a dendritic pattern; all

groups of all repeating units are attached to another repeating unit till the penultimate repeating unit of every branch, and the

groups of the terminal repeating units of all branches are attached to an atom or a functional group independently selected from the group consisting of hydrogen, tert-butyloxycarbonyl (Boc), and fluorenylmethyloxycarbonyl (Fmoc);
b) at least one monoclonal antibody;
c) phosphate buffer; and
d) sodium chloride,
wherein the monoclonal antibody to dendron molar ratio is in the range of 1:0.5-1:2 and the dendron stabilizes the monoclonal antibody in the formulation at a temperature of up to 55° C.

According to another embodiment, the present disclosure relates to a formulation comprising:
a) a dendron of Formula I,

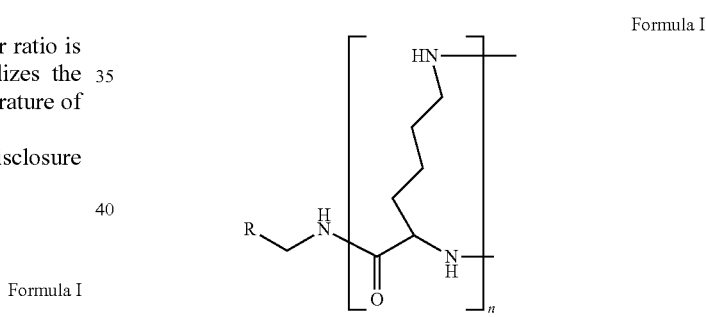

Formula I wherein R is selected from the group consisting of $C_{1-16}$ alkyl, $C_{5-22}$ aryl, $C_{1-16}$ alkoxy, $C_{1-16}$ haloalkyl, $C_{3-12}$ cycloalkyl, $C_{1-20}$ heteroaryl, $C_{1-20}$ heterocyclyl, $C_{2-16}$ alkenyl, $C_{2-16}$ alkynyl, —COOR$_a$, —C(O)R$_b$, —C(O)NR$_b$R$_c$, —NR$_d$R$_e$, —NR$_b$C(O)R$_c$, —OC(O)R$_b$, wherein R$_a$ is selected from the group consisting of hydrogen, $C_{1-16}$ alkyl, $C_{5-22}$ aryl, $C_{3-12}$ cycloalkyl, $C_{1-20}$ heteroaryl, $C_{1-20}$ heterocyclyl; R$_b$ and R$_c$ are independently selected from the group consisting of hydrogen, $C_{1-16}$ alkyl, $C_{5-22}$ aryl, $C_{1-16}$ haloalkyl, $C_{3-12}$ cycloalkyl, $C_{1-20}$ heteroaryl, $C_{1-20}$ heterocyclyl; R$_d$ and R$_e$ are independently selected from the group consisting of hydrogen, $C_{1-16}$ alkyl, $C_{5-22}$ aryl, $C_{1-16}$ haloalkyl, $C_{3-12}$ cycloalkyl, $C_{1-20}$ heteroaryl, $C_{1-20}$ heterocyclyl, wherein 'n' is in the range of 1-15; the branch growth follows a dendritic pattern; all

groups of all repeating units are attached to another repeating unit till the penultimate repeating unit of every branch, and the

groups of the terminal repeating units of all branches are attached to an atom or a functional group independently selected from the group consisting of hydrogen, tert-butyloxycarbonyl (Boc), and fluorenylmethyloxycarbonyl (Fmoc);
b) at least one monoclonal antibody;
c) phosphate buffer; and
d) sodium chloride,
wherein the monoclonal antibody to dendron molar ratio is in the range of 1:1-1:3 and the dendron stabilizes the monoclonal antibody in the formulation at a temperature of up to 55° C.

According to yet another embodiment, the present disclosure relates to a formulation comprising:
a) a dendron of Formula I,

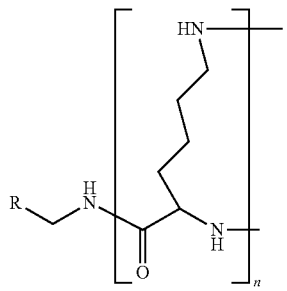

Formula I wherein R is selected from the group consisting of hydrogen, halogen, $C_{1-16}$ alkyl, $C_{5-22}$ aryl, $C_{1-16}$ alkoxy, $C_{1-16}$ haloalkyl, $C_{3-12}$ cycloalkyl, $C_{1-20}$ heteroaryl, $C_{1-20}$ heterocyclyl, $C_{2-16}$ alkenyl, $C_{2-16}$ alkynyl, —C(O)$R_b$, —C(O)NR$_b$R$_c$, —NR$_d$R$_e$, —NR$_b$C(O)R$_c$, —OC(O)R$_b$, wherein R$_b$ and R$_c$ are independently selected from the group consisting of hydrogen, $C_{1-16}$ alkyl, $C_{5-22}$ aryl, $C_{1-16}$ haloalkyl, $C_{3-12}$ cycloalkyl, $C_{1-20}$ heteroaryl, $C_{1-20}$ heterocyclyl; R$_d$ and R$_e$ are independently selected from the group consisting of hydrogen, $C_{1-16}$ alkyl, $C_{5-22}$ aryl, $C_{1-16}$ haloalkyl, $C_{3-12}$ cycloalkyl, $C_{1-20}$ heteroaryl, $C_{1-20}$ heterocyclyl,
wherein 'n' is in the range of 1-15; the branch growth follows a dendritic pattern; all

groups of all repeating units are attached to another repeating unit till the penultimate repeating unit of every branch, and the

groups of the terminal repeating units of all branches are attached to an atom or a functional group independently selected from the group consisting of hydrogen, tert-butyloxycarbonyl (Boc), and fluorenylmethyloxycarbonyl (Fmoc);
b) at least one monoclonal antibody;
c) phosphate buffer; and
d) sodium chloride,
wherein the monoclonal antibody to dendron molar ratio is in the range of 1:0.5-1:1.5 and the dendron stabilizes the monoclonal antibody in the formulation at a temperature of up to 55° C.

According to one embodiment, the present disclosure relates to a formulation comprising:
a) a dendron of Formula I,

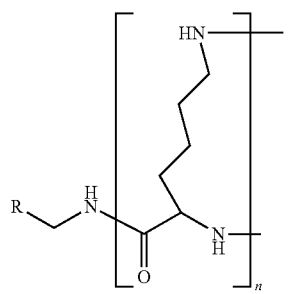

Formula I wherein R is selected from the group consisting of hydrogen, halogen, $C_{1-16}$ alkyl, $C_{5-22}$ aryl, $C_{1-16}$ alkoxy, $C_{1-16}$ haloalkyl, $C_{3-12}$ cycloalkyl, $C_{1-20}$ heteroaryl, $C_{1-20}$ heterocyclyl, $C_{2-16}$ alkenyl, $C_{2-16}$ alkynyl, —COOR$_a$, —C(O)R$_b$, —NR$_b$C(O)R$_c$, —OC(O)R$_b$, wherein R$_a$ is selected from the group consisting of hydrogen, $C_{1-16}$ alkyl, $C_{5-22}$ aryl, $C_{3-12}$ cycloalkyl, $C_{1-20}$ heteroaryl, $C_{1-20}$ heterocyclyl; R$_b$ and L are independently selected from the group consisting of hydrogen, $C_{1-16}$ alkyl, $C_{5-22}$ aryl, $C_{1-16}$ haloalkyl, $C_{3-12}$ cycloalkyl, $C_{1-20}$ heteroaryl, $C_{1-20}$ heterocyclyl,
wherein 'n' is in the range of 1-15; the branch growth follows a dendritic pattern; all

groups of all repeating units are attached to another repeating unit till the penultimate repeating unit of every branch, and the

groups of the terminal repeating units of all branches are attached to an atom or a functional group independently selected from the group consisting of hydrogen, tert-butyloxycarbonyl (Boc), and fluorenylmethyloxycarbonyl (Fmoc);
b) at least one monoclonal antibody;
c) phosphate buffer; and
d) sodium chloride,
wherein the monoclonal antibody to dendron molar ratio is in the range of 1:1-1:2 and the dendron stabilizes the monoclonal antibody in the formulation at a temperature of up to 55° C.

According to one embodiment, the present disclosure relates to a formulation comprising:
a) a dendron of Formula I,

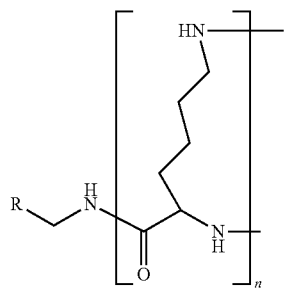

Formula I wherein R is selected from the group consisting of hydrogen, halogen, $C_{1-16}$ alkyl, $C_{5-22}$ aryl, $C_{1-16}$ alkoxy, $C_{1-16}$ haloalkyl, $C_{3-12}$ cycloalkyl, $C_{1-20}$ heteroaryl, $C_{1-20}$ heterocyclyl, $C_{2-16}$ alkenyl, $C_{2-16}$ alkynyl, —C(O)NR$_b$R$_c$, —NR$_d$R$_e$, —NR$_b$C(O)R$_c$, —OC(O)R$_b$, wherein R$_b$ and R$_c$ are independently selected from the group consisting of hydrogen, $C_{1-16}$ alkyl, $C_{5-22}$ aryl, $C_{1-16}$ haloalkyl, $C_{3-12}$ cycloalkyl, $C_{1-20}$ heteroaryl, $C_{1-20}$ heterocyclyl; R$_d$ and R$_e$ are independently selected from the group consisting of hydrogen, $C_{1-16}$ alkyl, $C_{5-22}$ aryl, $C_{1-16}$ haloalkyl, $C_{3-12}$ cycloalkyl, $C_{1-20}$ heteroaryl, $C_{1-20}$ heterocyclyl,
wherein 'n' is in the range of 1-15; the branch growth follows a dendritic pattern; all

groups of all repeating units are attached to another repeating unit till the penultimate repeating unit of every branch, and the

groups of the terminal repeating units of all branches are attached to an atom or a functional group independently selected from the group consisting of hydrogen, tert-butyloxycarbonyl (Boc), and fluorenylmethyloxycarbonyl (Fmoc);
b) at least one monoclonal antibody;
c) phosphate buffer; and
d) sodium chloride,
wherein the monoclonal antibody to dendron molar ratio is in the range of 1:0.5-1:2 and the dendron stabilizes the monoclonal antibody in the formulation at a temperature of up to 55° C.

According to another embodiment, the present disclosure relates to a formulation comprising:
a) a dendron of Formula I,

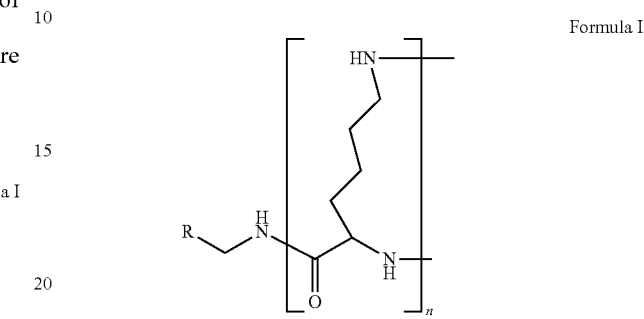

Formula I wherein R is selected from the group consisting of hydrogen, halogen, $C_{1-16}$ alkyl, $C_{1-16}$ alkoxy, $C_{3-12}$ cycloalkyl, $C_{1-20}$ heteroaryl, $C_{1-20}$ heterocyclyl, $C_{2-16}$ alkenyl, $C_{2-16}$ alkynyl, —COOR$_a$, —C(O)R$_b$, —C(O)NR$_b$R$_c$, —NR$_d$R$_e$, —NR$_b$C(O)R$_c$, —OC(O)R$_b$, wherein R$_a$ is selected from the group consisting of hydrogen, $C_{1-16}$ alkyl, $C_{5-22}$ aryl, $C_{3-12}$ cycloalkyl; R$_b$ and R$_c$ are independently selected from the group consisting of hydrogen, $C_{1-16}$ alkyl, $C_{5-22}$ aryl, $C_{1-16}$ haloalkyl, $C_{3-12}$ cycloalkyl, $C_{1-20}$ heteroaryl, $C_{1-20}$ heterocyclyl; R$_d$ and R$_e$ are independently selected from the group consisting of hydrogen, $C_{1-16}$ alkyl, $C_{5-22}$ aryl, $C_{1-16}$ haloalkyl, $C_{3-12}$ cycloalkyl, $C_{1-20}$ heteroaryl, $C_{1-20}$ heterocyclyl,
wherein 'n' is in the range of 1-15; the branch growth follows a dendritic pattern; all

groups of all repeating units are attached to another repeating unit till the penultimate repeating unit of every branch, and the

groups of the terminal repeating units of all branches are attached to an atom or a functional group independently selected from the group consisting of hydrogen, tert-butyloxycarbonyl (Boc), and fluorenylmethyloxycarbonyl (Fmoc);
b) at least one monoclonal antibody;
c) phosphate buffer; and
d) sodium chloride,
wherein the monoclonal antibody to dendron molar ratio is in the range of 1:1-1:3 and the dendron stabilizes the monoclonal antibody in the formulation at a temperature of up to 55° C.

According to yet another embodiment, the present disclosure relates to a formulation comprising:

a) a dendron of Formula I,

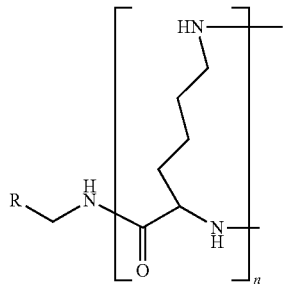

Formula I wherein R is selected from the group consisting of hydrogen, halogen, $C_{1-16}$ alkyl, $C_{5-22}$ aryl, $C_{1-16}$ alkoxy, $C_{1-16}$ haloalkyl, $C_{3-12}$ cycloalkyl, $C_{1-20}$ heteroaryl, $C_{1-20}$ heterocyclyl, $C_{2-16}$ alkynyl, —COOR$_a$, —C(O)R$_b$, —C(O)NR$_b$R$_c$, —NR$_d$R$_e$, —NR$_b$C(O)R$_c$, —OC(O)R$_b$, wherein R$_a$ is selected from the group consisting of hydrogen, $C_{1-16}$ alkyl, $C_{5-22}$ aryl, $C_{3-12}$ cycloalkyl, $C_{1-20}$ heteroaryl, $C_{1-20}$ heterocyclyl; R$_b$ and R$_c$ are independently selected from the group consisting of hydrogen, $C_{1-16}$ alkyl, $C_{5-22}$ aryl, $C_{1-16}$ haloalkyl, $C_{3-12}$ cycloalkyl, $C_{1-20}$ heteroaryl, $C_{1-20}$ heterocyclyl; R$_d$ and R$_e$ are independently selected from the group consisting of hydrogen, $C_{1-16}$ alkyl, $C_{5-22}$ aryl, $C_{1-16}$ haloalkyl, $C_{3-12}$ cycloalkyl, $C_{1-20}$ heteroaryl, $C_{1-20}$ heterocyclyl, wherein 'n' is in the range of 1-15; the branch growth follows a dendritic pattern; all

groups of all repeating units are attached to another repeating unit till the penultimate repeating unit of every branch, and the

groups of the terminal repeating units of all branches are attached to an atom or a functional group independently selected from the group consisting of hydrogen, tert-butyloxycarbonyl (Boc), and fluorenylmethyloxycarbonyl (Fmoc);

b) at least one monoclonal antibody;
c) phosphate buffer; and
d) sodium chloride, wherein the monoclonal antibody to dendron molar ratio is in the range of 1:0.5-1:2 and the dendron stabilizes the monoclonal antibody in the formulation at a temperature of up to 55° C.

According to yet another embodiment, the present disclosure relates to a formulation comprising:

a) a dendron of Formula I,

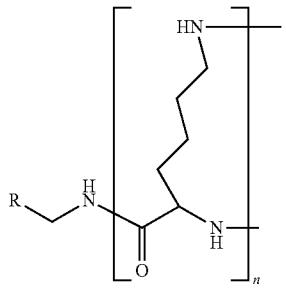

Formula I wherein R is selected from the group consisting of hydrogen, halogen, $C_{1-16}$ alkyl, $C_{5-22}$ aryl, $C_{1-16}$ alkoxy, $C_{1-16}$ haloalkyl, $C_{3-12}$ cycloalkyl, $C_{1-20}$ heteroaryl, $C_{1-20}$ heterocyclyl, $C_{2-16}$ alkenyl, $C_{2-16}$ alkynyl, —COOR$_a$, —C(O)R$_b$, —C(O)NR$_b$R$_c$, —NR$_d$R$_e$, —NR$_b$C(O)R$_c$, —OC(O)R$_b$, wherein R$_a$ is selected from the group consisting of hydrogen, $C_{1-16}$ alkyl, $C_{5-22}$ aryl; R$_b$ and R$_c$ are independently selected from the group consisting of hydrogen, $C_{1-16}$ alkyl, $C_{5-22}$ aryl, $C_{1-16}$ haloalkyl; R$_d$ and R$_e$ are independently selected from the group consisting of hydrogen, $C_{1-16}$ alkyl, $C_{5-22}$ aryl, $C_{1-16}$ haloalkyl, wherein 'n' is in the range of 1-15; the branch growth follows a dendritic pattern; all

groups of all repeating units are attached to another repeating unit till the penultimate repeating unit of every branch, and the

groups of the terminal repeating units of all branches are attached to an atom or a functional group independently selected from the group consisting of hydrogen, tert-butyloxycarbonyl (Boc), and fluorenylmethyloxycarbonyl (Fmoc);

b) at least one monoclonal antibody;
c) phosphate buffer; and
d) sodium chloride, wherein the monoclonal antibody to dendron molar ratio is in the range of 1:0.5-1:3 and the dendron stabilizes the monoclonal antibody in the formulation at a temperature of up to 55° C.

According to one embodiment, the present disclosure relates to a formulation comprising:

a) a dendron of Formula I,

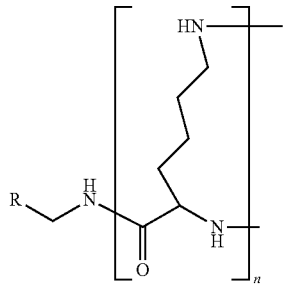

Formula I wherein R is selected from the group consisting of hydrogen, halogen, $C_{1-16}$ alkyl, $C_{5-22}$ aryl, $C_{1-16}$ alkoxy, $C_{1-16}$ haloalkyl, $C_{3-12}$ cycloalkyl, $C_{1-20}$ heteroaryl, $C_{1-20}$ heterocyclyl, $C_{2-16}$ alkenyl, $C_{2-16}$ alkynyl, —COOR$_a$, wherein R$_a$ is selected from the group consisting of hydrogen, $C_{1-16}$ alkyl, $C_{5-22}$ aryl, $C_{3-12}$ cycloalkyl, $C_{1-20}$ heteroaryl, $C_{1-20}$ heterocyclyl, wherein 'n' is in the range of 1-15; the branch growth follows a dendritic pattern; all

groups of all repeating units are attached to another repeating unit till the penultimate repeating unit of every branch, and the

groups of the terminal repeating units of all branches are attached to an atom or a functional group independently selected from the group consisting of hydrogen, tert-butyloxycarbonyl (Boc), and fluorenylmethyloxycarbonyl (Fmoc);

b) at least one monoclonal antibody;

c) phosphate buffer; and d) sodium chloride, wherein the monoclonal antibody to dendron molar ratio is in the range of 1:0.5-1:2 and the dendron stabilizes the monoclonal antibody in the formulation at a temperature of up to 55° C.

According to another embodiment, the present disclosure relates to a formulation comprising:

a) a dendron of Formula I,

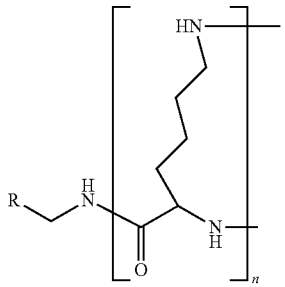

Formula I wherein R is selected from the group consisting of hydrogen, halogen, $C_{1-16}$ alkyl, $C_{5-22}$ aryl, $C_{2-16}$ alkenyl, $C_{2-16}$ alkynyl, —COOR$_a$, —C(O)R$_b$, —C(O)NR$_b$R$_c$, —NR$_d$R$_e$, —NR$_b$C(O)R$_c$, —OC(O)R$_b$, wherein R$_a$ is selected from the group consisting of hydrogen, $C_{1-16}$ alkyl, $C_{5-22}$ aryl, $C_{3-12}$ cycloalkyl, $C_{1-20}$ heteroaryl, $C_{1-20}$ heterocyclyl; R$_b$ and R$_c$ are independently selected from the group consisting of hydrogen, $C_{1-16}$ alkyl, $C_{5-22}$ aryl, $C_{1-16}$ haloalkyl, $C_{3-12}$ cycloalkyl, $C_{1-20}$ heteroaryl, $C_{1-20}$ heterocyclyl; R$_d$ and R$_e$ are independently selected from the group consisting of hydrogen, $C_{1-16}$ alkyl, $C_{5-22}$ aryl, $C_{1-16}$ haloalkyl, $C_{3-12}$ cycloalkyl, $C_{1-20}$ heteroaryl, $C_{1-20}$ heterocyclyl, wherein 'n' is in the range of 1-15; the branch growth follows a dendritic pattern; all

groups of all repeating units are attached to another repeating unit till the penultimate repeating unit of every branch, and the

groups of the terminal repeating units of all branches are attached to an atom or a functional group independently selected from the group consisting of hydrogen and tert-butyloxycarbonyl (Boc);

b) at least one monoclonal antibody;

c) phosphate buffer; and d) sodium chloride, wherein the monoclonal antibody to dendron molar ratio is in the range of 1:1-1:3 and the dendron stabilizes the monoclonal antibody in the formulation at a temperature of up to 55° C.

According to yet another embodiment, the present disclosure relates to a formulation comprising:

a) a dendron of Formula I,

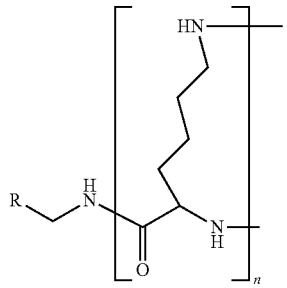

Formula I wherein R is selected from the group consisting of $C_{2-16}$ alkenyl, $C_{2-16}$ alkynyl, —$COOR_a$, —$C(O)R_b$, —$C(O)NR_bR_c$, —$NR_dR_e$, —$NR_bC(O)R_c$, —$OC(O)R_b$, wherein $R_a$ is selected from the group consisting of hydrogen, $C_{1-16}$ alkyl, $C_{5-22}$ aryl, $C_{3-12}$ cycloalkyl, $C_{1-20}$ heteroaryl, $C_{1-20}$ heterocyclyl; $R_b$ and $R_c$ are independently selected from the group consisting of hydrogen, $C_{1-16}$ alkyl, $C_{5-22}$ aryl, $C_{1-16}$ haloalkyl, $C_{3-12}$ cycloalkyl, $C_{1-20}$ heteroaryl, $C_{1-20}$ heterocyclyl; $R_d$ and $R_e$ are independently selected from the group consisting of hydrogen, $C_{1-16}$ alkyl, $C_{5-22}$ aryl, $C_{1-16}$ haloalkyl, $C_{3-12}$ cycloalkyl, $C_{1-20}$ heteroaryl, $C_{1-20}$ heterocyclyl, wherein 'n' is in the range of 1-15; the branch growth follows a dendritic pattern; all

groups of all repeating units are attached to another repeating unit till the penultimate repeating unit of every branch, and the

groups of the terminal repeating units of all branches are attached to an atom or a functional group independently selected from the group consisting of hydrogen, tert-butyloxycarbonyl (Boc), and fluorenylmethyloxycarbonyl (Fmoc);

b) at least one monoclonal antibody;

c) phosphate buffer; and d) sodium chloride, wherein the monoclonal antibody to dendron molar ratio is in the range of 1:0.5-1:3 and the dendron stabilizes the monoclonal antibody in the formulation at a temperature of up to 55° C.

According to one embodiment, the present disclosure relates to a formulation comprising:

a) a dendron of Formula I,

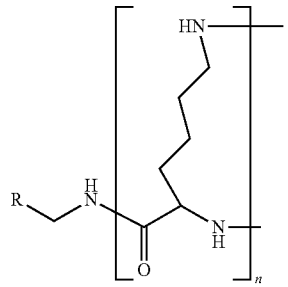

Formula I wherein R is selected from the group consisting of $C_{2-16}$ alkynyl, —$COOR_a$, —$C(O)R_b$, —$C(O)NR_bR_c$, —$NR_dR_e$, —$NR_bC(O)R_c$, —$OC(O)R_b$, wherein $R_a$ is selected from the group consisting of hydrogen, $C_{1-16}$ alkyl, $C_{5-22}$ aryl, $C_{3-12}$ cycloalkyl, $C_{1-20}$ heteroaryl, $C_{1-20}$ heterocyclyl; $R_b$ and $R_c$ are independently selected from the group consisting of hydrogen, $C_{1-16}$ alkyl, $C_{5-22}$ aryl, $C_{1-16}$ haloalkyl, $C_{3-12}$ cycloalkyl, $C_{1-20}$ heteroaryl, $C_{1-20}$ heterocyclyl; $R_d$ and $R_e$ are independently selected from the group consisting of hydrogen, $C_{1-16}$ alkyl, $C_{5-22}$ aryl, $C_{1-16}$ haloalkyl, $C_{3-12}$ cycloalkyl, $C_{1-20}$ heteroaryl, $C_{1-20}$ heterocyclyl, wherein 'n' is in the range of 1-15; the branch growth follows a dendritic pattern; all

groups of all repeating units are attached to another repeating unit till the penultimate repeating unit of every branch, and the

groups of the terminal repeating units of all branches are attached to an atom or a functional group independently selected from the group consisting of hydrogen, tert-butyloxycarbonyl (Boc), and fluorenylmethyloxycarbonyl (Fmoc);

b) at least one monoclonal antibody;

c) phosphate buffer; and d) sodium chloride, wherein the monoclonal antibody to dendron molar ratio is in the range of 1:1-1:3 and the dendron stabilizes the monoclonal antibody in the formulation at a temperature of up to 55° C.

According to another embodiment, the present disclosure relates to a formulation comprising:

a) a dendron of Formula I,

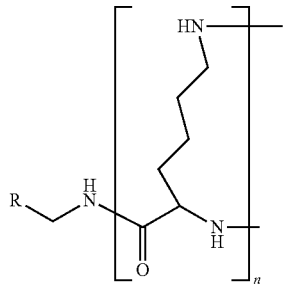

Formula I wherein R is selected from the group consisting of $C_{2-16}$ alkynyl, —$COOR_a$, —$C(O)R_b$, —$C(O)NR_bR_c$, —$NR_dR_e$, —$NR_bC(O)R_c$, wherein $R_a$ is selected from the group consisting of hydrogen, $C_{1-16}$ alkyl, $C_{5-22}$ aryl, $C_{3-12}$ cycloalkyl, $C_{1-20}$ heteroaryl, $C_{1-20}$ heterocyclyl; $R_b$ and $R_c$ are independently selected from the group consisting of hydrogen, $C_{1-16}$ alkyl, $C_{5-22}$ aryl, $C_{1-16}$ haloalkyl, $C_{3-12}$ cycloalkyl, $C_{1-20}$ heteroaryl, $C_{1-20}$ heterocyclyl; $R_d$ and $R_e$ are independently selected from the group consisting of hydrogen, $C_{1-16}$ alkyl, $C_{5-22}$ aryl, $C_{1-16}$ haloalkyl, $C_{3-12}$ cycloalkyl, $C_{1-20}$ heteroaryl, $C_{1-20}$ heterocyclyl, wherein 'n' is in the range of 1-15; the branch growth follows a dendritic pattern; all

groups of all repeating units are attached to another repeating unit till the penultimate repeating unit of every branch, and the

groups of the terminal repeating units of all branches are attached to an atom or a functional group independently selected from the group consisting of hydrogen, tert-butyloxycarbonyl (Boc), and fluorenylmethyloxycarbonyl (Fmoc);

b) at least one monoclonal antibody;

c) phosphate buffer; and d) sodium chloride, wherein the monoclonal antibody to dendron molar ratio is in the range of 1:0.5-1:2 and the dendron stabilizes the monoclonal antibody in the formulation at a temperature of up to 55° C.

According to yet another embodiment, the present disclosure relates to a formulation comprising:

a) a dendron of Formula I,

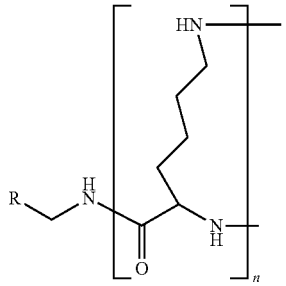

Formula I wherein R is selected from the group consisting of $C_{2-16}$ alkynyl, —$COOR_a$, —$C(O)R_b$, —$C(O)NR_bR_c$, —$NR_dR_e$, wherein $R_a$ is selected from the group consisting of hydrogen, $C_{1-16}$ alkyl, $C_{5-22}$ aryl, $C_{3-12}$ cycloalkyl, $C_{1-20}$ heteroaryl, $C_{1-20}$ heterocyclyl; $R_b$ and $R_c$ are independently selected from the group consisting of hydrogen, $C_{1-16}$ alkyl, $C_{5-22}$ aryl, $C_{1-16}$ haloalkyl, $C_{3-12}$ cycloalkyl, $C_{1-20}$ heteroaryl, $C_{1-20}$ heterocyclyl; $R_d$ and $R_e$ are independently selected from the group consisting of hydrogen, $C_{1-16}$ alkyl, $C_{5-22}$ aryl, $C_{1-16}$ haloalkyl, $C_{3-12}$ cycloalkyl, $C_{1-20}$ heteroaryl, $C_{1-20}$ heterocyclyl, wherein 'n' is in the range of 1-15; the branch growth follows a dendritic pattern; all

groups of all repeating units are attached to another repeating unit till the penultimate repeating unit of every branch, and the

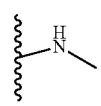

groups of the terminal repeating units of all branches are attached to an atom or a functional group independently selected from the group consisting of hydrogen, tert-butyloxycarbonyl (Boc), and fluorenylmethyloxycarbonyl (Fmoc);

b) at least one monoclonal antibody;

c) phosphate buffer; and d) sodium chloride, wherein the monoclonal antibody to dendron molar ratio is in the range of 1:1-1:3 and the dendron stabilizes the monoclonal antibody in the formulation at a temperature of up to 55° C.

According to one embodiment, the present disclosure relates to a formulation comprising:

a) a dendron of Formula I,

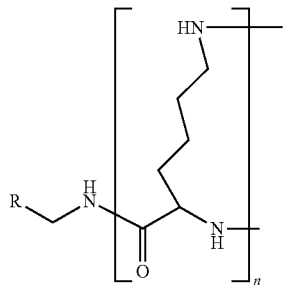

Formula I wherein R is selected from the group consisting of $C_{2-16}$ alkynyl, —$COOR_a$, —$C(O)R_b$, —$C(O)NR_bR_c$, wherein $R_a$ is selected from the group consisting of hydrogen, $C_{1-16}$ alkyl, $C_{5-22}$ aryl, $C_{3-12}$ cycloalkyl, $C_{1-20}$ heteroaryl, $C_{1-20}$ heterocyclyl; $R_b$ and $R_c$ are independently selected from the group consisting of hydrogen, $C_{1-16}$ alkyl, $C_{5-22}$ aryl, $C_{1-16}$ haloalkyl, $C_{3-12}$ cycloalkyl, $C_{1-20}$ heteroaryl, $C_{1-20}$ heterocyclyl, wherein 'n' is in the range of 1-15; the branch growth follows a dendritic pattern; all

groups of all repeating units are attached to another repeating unit till the penultimate repeating unit of every branch, and the

groups of the terminal repeating units of all branches are attached to an atom or a functional group independently selected from the group consisting of hydrogen, tert-butyloxycarbonyl (Boc), and fluorenylmethyloxycarbonyl (Fmoc);

b) at least one monoclonal antibody;

c) phosphate buffer; and d) sodium chloride, wherein the monoclonal antibody to dendron molar ratio is in the range of 1:0.5-1:2 and the dendron stabilizes the monoclonal antibody in the formulation at a temperature of up to 55° C.

According to another embodiment, the present disclosure relates to a formulation comprising:

a) a dendron of Formula I,

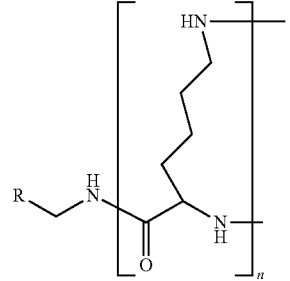

Formula I wherein R is selected from the group consisting of $C_{2-16}$ alkynyl, —$COOR_a$, —$C(O)R_b$, wherein $R_a$ is selected from the group consisting of hydrogen, $C_{1-16}$ alkyl, $C_{5-22}$ aryl, $C_{3-12}$ cycloalkyl, $C_{1-20}$ heteroaryl, $C_{1-20}$ heterocyclyl; $R_b$ is selected from the group consisting of hydrogen, $C_{1-16}$ alkyl, $C_5$-22 aryl, $C_{1-16}$ haloalkyl, $C_{3-12}$ cycloalkyl, $C_{1-20}$ heteroaryl, $C_{1-20}$ heterocyclyl, wherein 'n' is in the range of 1-15; the branch growth follows a dendritic pattern; all

groups of all repeating units are attached to another repeating unit till the penultimate repeating unit of every branch, and the

groups of the terminal repeating units of all branches are attached to an atom or a functional group independently selected from the group consisting of hydrogen, tert-butyloxycarbonyl (Boc), and fluorenylmethyloxycarbonyl (Fmoc);

b) at least one monoclonal antibody;

c) phosphate buffer; and d) sodium chloride, wherein the monoclonal antibody to dendron molar ratio is in the range of 1:1-1:3 and the dendron stabilizes the monoclonal antibody in the formulation at a temperature of up to 55° C.

According to yet another embodiment, the present disclosure relates to a formulation comprising:

a) a dendron of Formula I,

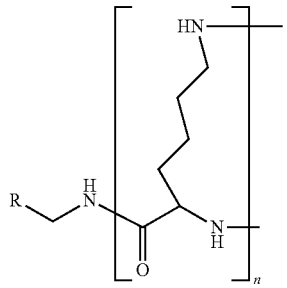

Formula I wherein R is selected from the group consisting of $C_{2-16}$ alkynyl and —$COOR_a$, wherein $R_a$ is selected from the group consisting of hydrogen, $C_{1-16}$ alkyl, $C_{5-22}$ aryl, $C_{3-12}$ cycloalkyl, $C_{1-20}$ heteroaryl, $C_{1-20}$ heterocyclyl, wherein 'n' is in the range of 1-15; the branch growth follows a dendritic pattern; all

groups of all repeating units are attached to another repeating unit till the penultimate repeating unit of every branch, and the

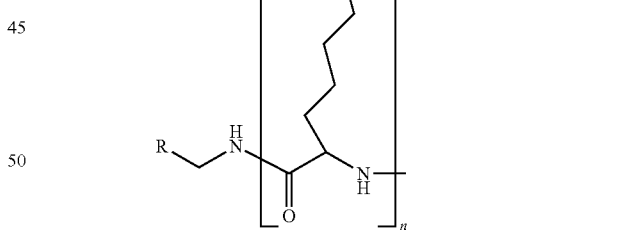

groups of the terminal repeating units of all branches are attached to an atom or a functional group independently selected from the group consisting of hydrogen, tert-butyloxycarbonyl (Boc), and fluorenylmethyloxycarbonyl (Fmoc);

b) at least one monoclonal antibody;

c) phosphate buffer; and d) sodium chloride, wherein the monoclonal antibody to dendron molar ratio is in the range of 1:1-1:3 and the dendron stabilizes the monoclonal antibody in the formulation at a temperature of up to 55° C.

According to one embodiment, the present disclosure relates to a formulation comprising:

a) a dendron of Formula I,

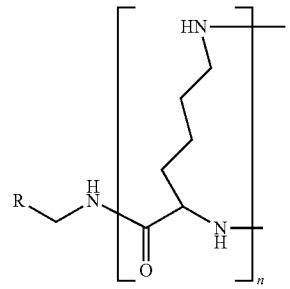

Formula I wherein R is ethynyl, wherein 'n' is 1, and the

groups are attached to hydrogen;

b) at least one monoclonal antibody;

c) phosphate buffer; and d) sodium chloride, wherein the monoclonal antibody to dendron molar ratio is in the range of 1:0.5-1:3 and the dendron stabilizes the monoclonal antibody in the formulation at a temperature of up to 55° C.

According to another embodiment, the present disclosure relates to a formulation comprising:

a) a dendron of Formula I,

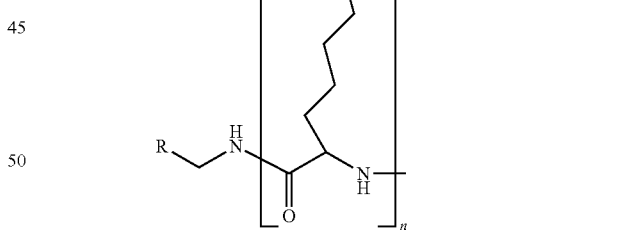

Formula I wherein R is ethynyl, wherein 'n' is 3; the branch growth follows a dendritic pattern; all

groups of all repeating units are attached to another repeating unit till the penultimate repeating unit of every branch, and the

groups of the terminal repeating units of all branches are attached to hydrogen;
b) at least one monoclonal antibody;
c) phosphate buffer; and
d) sodium chloride,
wherein the monoclonal antibody to dendron molar ratio is in the range of 1:0.5-1:3 and the dendron stabilizes the monoclonal antibody in the formulation at a temperature of up to 55° C.

According to yet another embodiment, the present disclosure relates to a formulation comprising:
a) a dendron of Formula I,

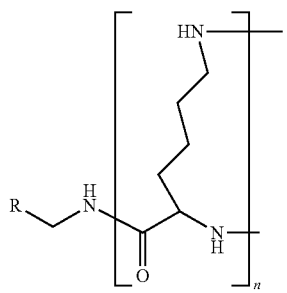

Formula I wherein R is ethynyl,
wherein 'n' is 7; the branch growth follows a dendritic pattern; all

groups of all repeating units are attached to another repeating unit till the penultimate repeating unit of every branch, and the

groups of the terminal repeating units of all branches are attached to hydrogen;
b) at least one monoclonal antibody;
c) phosphate buffer; and
d) sodium chloride,
wherein the monoclonal antibody to dendron molar ratio is in the range of 1:0.5-1:3 and the dendron stabilizes the monoclonal antibody in the formulation at a temperature of up to 55° C.

According to one embodiment, the present disclosure relates to a formulation as described herein, wherein the formulation has a pH in the range of 5.5-8.

According to another embodiment, the present disclosure relates to a formulation wherein, the bio-therapeutics remain stable at high temperatures of up to 55° C. without considerable degradation, and can be used for curative purposes.

According to another embodiment, the present disclosure relates to a process for the preparation of a formulation comprising:
a) a dendron of Formula I,

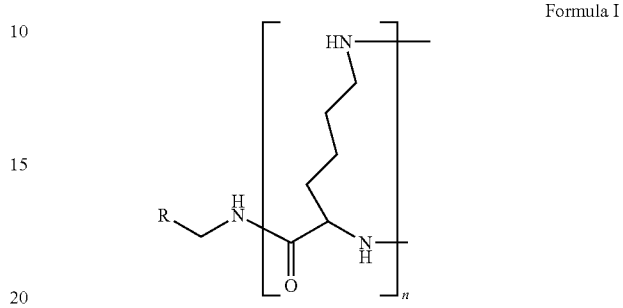

Formula I wherein R is selected from the group consisting of hydrogen, halogen, $C_{1-16}$ alkyl, $C_{5-22}$ aryl, $C_{1-16}$ alkoxy, $C_{1-16}$ haloalkyl, $C_{3-12}$ cycloalkyl, $C_{1-20}$ heteroaryl, $C_{1-20}$ heterocyclyl, $C_{2-16}$ alkenyl, $C_{2-16}$ alkynyl, —COOR$_a$, —C(O)R$_b$, —C(O)NR$_b$R$_c$, —NR$_d$R$_e$, —NR$_b$C(O)R$_c$, —OC(O)R$_b$, wherein R$_a$ is selected from the group consisting of hydrogen, $C_{1-16}$ alkyl, $C_{5-22}$ aryl, $C_{3-12}$ cycloalkyl, $C_{1-20}$ heteroaryl, $C_{1-20}$ heterocyclyl; R$_b$ and R$_c$ are independently selected from the group consisting of hydrogen, $C_{1-16}$ alkyl, $C_{5-22}$ aryl, $C_{1-16}$ haloalkyl, $C_{3-12}$ cycloalkyl, $C_{1-20}$ heteroaryl, $C_{1-20}$ heterocyclyl; R$_d$ and R$_e$ are independently selected from the group consisting of hydrogen, $C_{1-16}$ alkyl, $C_{5-22}$ aryl, $C_{1-16}$ haloalkyl, $C_{3-12}$ cycloalkyl, $C_{1-20}$ heteroaryl, $C_{1-20}$ heterocyclyl, wherein 'n' is in the range of 1-15; the branch growth follows a dendritic pattern; all

groups of all repeating units are attached to another repeating unit till the penultimate repeating unit of every branch, and the

groups of the terminal repeating units of all branches are attached to an atom or a functional group independently selected from the group consisting of hydrogen, tert-butyloxycarbonyl (Boc), and fluorenylmethyloxycarbonyl (Fmoc);
b) at least one bio-therapeutic;
c) at least one buffer solution; and
d) at least one salt,
wherein the bio-therapeutic to dendron molar ratio is in the range of 1:0.5-1:3 and the dendron stabilizes the bio-therapeutic in the formulation at a temperature of up to 55° C.; the process comprising the steps of: (a) contacting at least one buffer solution and at least one salt solution with at least one bio-therapeutic to obtain a mixture; (b) contacting the mixture from step (a) with the dendron to obtain the formulation.

According to another embodiment, the present disclosure relates to a process for the preparation of a formulation comprising:
a) a dendron of Formula I,

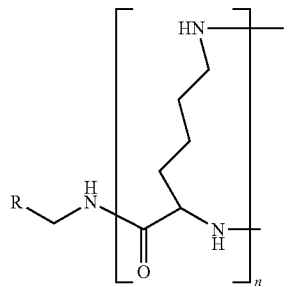

Formula I wherein R is selected from the group consisting of hydrogen, halogen, $C_{1-16}$ alkyl, $C_{5-22}$ aryl, $C_{1-16}$ alkoxy, $C_{1-16}$ haloalkyl, $C_{3-12}$ cycloalkyl, $C_{1-20}$ heteroaryl, $C_{1-20}$ heterocyclyl, $C_{2-16}$ alkenyl, $C_{2-16}$ alkynyl, —$COOR_a$, —$C(O)R_b$, —$C(O)NR_bR_c$, —$NR_dR_e$, —$NR_bC(O)R_c$, —$OC(O)R_b$, wherein $R_a$ is selected from the group consisting of hydrogen, $C_{1-16}$ alkyl, $C_{5-22}$ aryl, $C_{3-12}$ cycloalkyl, $C_{1-20}$ heteroaryl, $C_{1-20}$ heterocyclyl; $R_b$ and $R_c$ are independently selected from the group consisting of hydrogen, $C_{1-16}$ alkyl, $C_{5-22}$ aryl, $C_{1-16}$ haloalkyl, $C_{3-12}$ cycloalkyl, $C_{1-20}$ heteroaryl, $C_{1-20}$ heterocyclyl; $R_d$ and $R_e$ are independently selected from the group consisting of hydrogen, $C_{1-16}$ alkyl, $C_{5-22}$ aryl, $C_{1-16}$ haloalkyl, $C_{3-12}$ cycloalkyl, $C_{1-20}$ heteroaryl, $C_{1-20}$ heterocyclyl, wherein 'n' is in the range of 1-15; the branch growth follows a dendritic pattern; all

groups of all repeating units are attached to another repeating unit till the penultimate repeating unit of every branch, and the

groups of the terminal repeating units of all branches are attached to an atom or a functional group independently selected from the group consisting of hydrogen, tert-butyloxycarbonyl (Boc), and fluorenylmethyloxycarbonyl (Fmoc);
b) at least one bio-therapeutic;
c) at least one buffer solution; and
d) at least one salt,
wherein the bio-therapeutic to dendron molar ratio is in the range of 1:0.5-1:3 and the dendron stabilizes the bio-therapeutic in the formulation at a temperature of up to 55° C.; the process comprising the steps of: (a) contacting at least one buffer solution, at least one anti-bacterial agent selected from the group consisting of sodium azide, thymol, benzalkonium chloride, and glycerol, and at least one salt solution with at least one bio-therapeutic at a temperature in the range of 20-30° C., to obtain a mixture; (b) contacting the mixture from step (a) with the dendron by gel filtration chromatography based buffer exchange at a temperature in the range of 20-30° C., to obtain the formulation.

EXAMPLES

The following examples provide the details about the synthesis of the dendrons and various analyses carried out on the formulation. It should be understood the following is representative only, and that the invention is not limited by the details set forth in these examples.

Example 1

Synthesis of Dendrons and Related Intermediates

Figure 11:
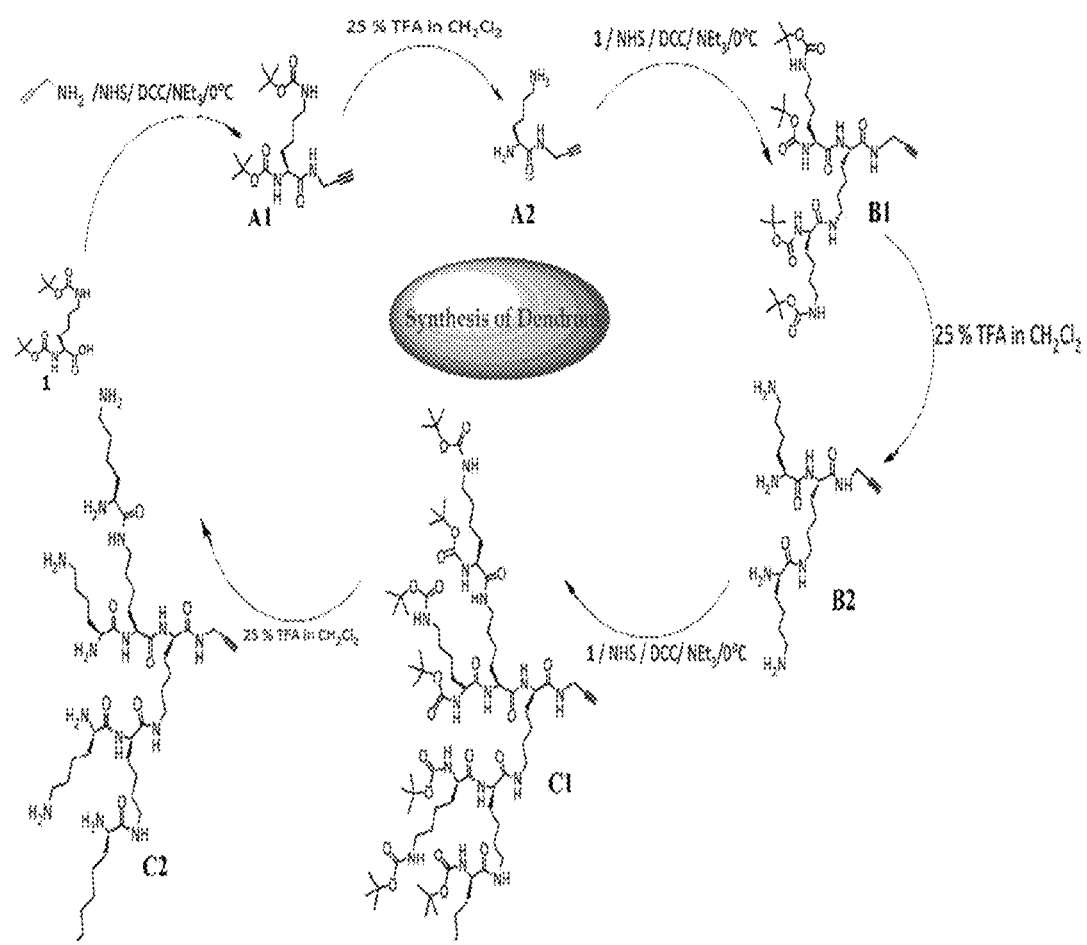
FIG. 11 is an illustration of a synthesis of dendrons carried out in accordance with an exemplary synthetic scheme.

The synthesis of dendrons was carried out in accordance with the following synthetic scheme (FIG. 11). The detailed general procedure for each step is described below.
Scheme 1
Materials and methods: All amino acids used were of L-configuration. Unless otherwise stated, all reagents were used without further purification. All solvents employed in the reactions were distilled or dried from appropriate drying agent prior to use. Amino acid L-Lysine, was purchased from SRL India. Reactions were monitored wherever possible by thin layer chromatography (TLC). Purification of compounds was done by silica gel column chromatography. Silica gel G (Merck) was used for TLC and column chromatography was done on silica gel (100-200 mesh) columns, which were generally made from slurry in hexane, hexane/ethyl acetate or dichloromethane. Analytical HPLC was carried out using Eclipse XDB-C18 column and acetonitrile/water as the solvent system. Detailed procedures have been described earlier.[4-6]
a) General Procedure for the Boc-Protection
To an ice cold and well-stirred solution of L-Lysine 0.0 mmol) in IN aq. NaOH, drop wise addition of Boc anhydride (2.2 mmol) was done over a period of 1 hr. The reaction mixture was stirred overnight, washed with hexane and acidified with saturated aq. solution of $KHSO_4$ to make the pH=2. The N-protected amino acid was extracted with ethyl acetate. The organic layer was collected, dried over anhydrous $Na_2SO_4$, filtered and evaporated to obtain the N-protected amino acid in quantitative yields.
b) General Procedure for the Peptide Coupling Reaction
To an ice-cooled and well stirred solution of N-protected amino acid (1.0 mmoles) in dry dichloromethane, was added N-hydroxysuccinimide (NHS) (1.2 mmol), dicyclohexylcarbodiimide (DCC) (1.2 mmol) and stirred for 10 min. To this mixture was added an amine component (1.2 mmol) in dichloromethane and triethylamine (1.2 mmol). The reaction mixture was stirred overnight, filtered and the filtrate was washed with 0.2 N $H_2SO_4$, water and finally with saturated aqueous $NaHCO_3$ solution. The organic layer was separated, dried over anhydrous $Na_2SO_4$, filtered and evaporated. Silica gel column chromatographic purification yielded the products in approximately 75-95% yields.
c) General Procedure for the Boc-Deprotection
To an ice-cooled solution of the Boc-protected compound (1 mmol) was added 25% solution of trifluroacetic acid TFA (40 mmol) in dry dichloromethane and stirred at room temperature for 3 hours. The reaction mixture was subjected to high vacuum, redissolved in ethylacetate/dichloromethane and washed with aqueous sodium carbonate. The organic layer was dried over anhydrous $Na_2SO_4$ and evaporated.

All dendrons and related intermediates were characterized by $^1H$ NMR, $^{13}C$ NMR, IR and HRMS. Purity of the compounds was analyzed by analytical HPLC (Agilent Technologies 1200 series, Santa Clara, USA) equipped with Eclipse XDB-C18 reversed phase column using acetonitrile/water as the solvent system.

d) Characterization Data

First generation dendron A1 (Boc-protected intermediate): Synthesized using general procedure (a) wherein N-protected amino acid was Boc-Lys(Boc)-OH and amine component was propargyl amine.

Yield: 94%; $[\alpha]_D$: −1.8 (c=0.38, $CHCl_3$)

NMR ($CDCl_3$, 300 MHz) δ 1.38-1.70 (s+m, 24H), 2.20 (t, J=2.4 Hz, 1H), 3.10 (m, 2H), 4.04 (m, 3H), 4.56 (br s, 1H), 5.03 (br d, 1H), 6.46 (br s, 1H); $^{13}C$ NMR (CDCl3, 75 MHz): δ 22.5, 28.2, 28.3, 28.9, 29.5, 32.0, 39.9, 54.1, 71.4, 79.0, 79.3, 80.0, 155.8, 156.1, 172.1; IR (KBr) 3333, 2977, 2935, 2866, 1687, 1524, 1453, 1376, 1249, 1171 $cm^{-1}$; HRMS calculated for $C_{19}H_{33}N_3NaO_5$ m/z 406.2318, found m/z 406.2311.

First generation dendron A2: Prepared using general procedure (b) from A1.

Yield: 95%; $[\alpha]_D$: +7.0 (c=0.1, MeOH)

$^1H$ NMR ($D_2O$, 300 MHz) δ 1.33-1.48 (m, 2H), 1.59-1.71 (m, 2H), 1.79-1.92 (m, 2H), 2.57 (s, 1H), 2.93 (t, 2H, J=7.2 Hz), 3.89-4.08 (m, 3H); $^{13}C$ NMR ($D_2O$, 75 MHz): δ 21.2, 26.3, 28.9, 30.2, 39.0, 53.0, 72.2, 79.0, 169.4; IR (KBr): 3673, 3562, 3458, 3362, 2988, 2317, 2058, 1684, 1508, 1185, $cm^{-1}$

HRMS calculated for $C_9H_{18}N_3O$ m/z 184.1450, found m/z 184.1444.

Second generation dendron B1: Prepared using general procedure (a) wherein N-protected amino acid was Boc-Lys(Boc)-OH and amine component was compound A2.

Yield: 87%; $[\alpha]_D$: −45.00 (c=0.39, $CHCl_3$)

$^1H$ NMR ($CDCl_3$, 300 MHz) δ 1.37-1.85 (s+m, 54H), 2.25 (s, 1H), 3.10 (m, 6H), 4.02 (s, 2H), 4.09-4.45 (m, 3H), 4.70-5.00 (m, 2H), 5.60 (br s, 1H), 5.95 (br s, 1H), 7.14 (br d, 2H), 7.43 (br s, 1H); $^{13}C$ NMR ($CDCl_3$, 75 MHz): δ 14.1, 22.1, 22.6, 22.7, 22.8, 28.4, 28.5, 29.1, 29.3, 29.5, 29.7, 30.6, 31.9, 32.6, 38.2, 39.9, 40.2, 53.1, 54.4, 71.6, 79.1, 79.5, 79.9, 80.2, 156.2, 171.5, 173.5; IR (KBr) 3340, 2932, 2862, 1691, 1651, 1527, 1450, 1372, 1249, 1169 $cm^{-1}$; HRMS calculated for $C_{41}H_{73}N_7O_{11}Na$ m/z 862.5266, found m/z 862.5262.

Second generation dendron B2: Prepared using general procedure (b) from B1.

Yield: 94%; $[\alpha]_D$: +9.0 (c=0.1, MeOH)

$^1H$ NMR ($D_2O$, 300 MHz) δ 1.17-1.58 (m, 18H), 2.54 (s, 1H), 2.92 (br s, 3H), 3.09-3.41 (m, 3H), 3.56-4.25 (m, 5H); $^{13}C$ NMR ($D_2O$, 75 MHz): δ 20.9, 21.2, 22.3, 26.3, 27.7, 28.7, 30.3, 38.9, 52.6, 53.0, 54.0, 71.8, 79.2, 110.4, 114.3, 118.1, 122.2, 162.5, 163.0, 169.4, 173.2; IR (KBr): 3711, 3647, 3441, 2924, 2334, 2037, 1682, 1201, 1001, $cm^{-1}$

HRMS calculated for $C_{21}H_{41}N_7O_3$ m/z 440.3349, found m/z 440.3342.

Third generation dendron C1:

Yield: 75%; $[\alpha]_D$: +28.66 (c=0.1, MeOH).

$^1H$ NMR (300 MHz, $CDCl_3$): δ 1.15-2.05 (br m, 114H), 2.20 (s, 1H), 2.95-3.70 (br m, 14H), 3.90-4.60 (br m, 9H), 4.72-5.25 (br m, 4H), 5.52-6.18 (br m, 4H), 6.68-7.20 (br m, 2H), 7.32-7.90 (br m, 5H); $^{13}C$ NMR (75 MHz, $CDCl_3$): δ 14.1, 22.7, 24.9, 25.6, 28.5, 29.7, 31.7, 31.9, 32.7, 33.9, 38.8, 39.9, 40.3, 53.0, 54.3, 71.4, 79.0, 79.9, 156.3, 172.6, 172.9, 173.6, 174.2; IR (KBr): 3325, 3082, 2976, 2934, 2861, 2247, 1693, 1649, 1527, 1452, 1392, 1367, 1249, 1171 $cm^{-1}$. (HRMS): calculated for $C_{85}H_{153}N_{15}O_{23}Na$ m/z 1775.1161, found m/z 1775.1158.

Third generation dendron C2:

Yield: 92%; $[\alpha]_D$: +2.6 (c=0.1, MeOH)

$^1H$ NMR ($D_2O$, 300 MHz) δ 0.95-1.80 (m, 42H), 2.26 (s, 1H), 2.67 (br s, 8H), 2.87 (br s, 6H), 3.52-3.79 (m, 6H), 3.81-4.05 (m, 3H); $^{13}C$ NMR ($D_2O$, 125 MHz): δ 6.9, 12.0, 16.2, 17.7, 21.3, 22.4, 26.3, 27.9, 28.7, 30.4, 38.9, 42.5, 52.7, 53.1, 54.3, 71.9, 79.4, 116.5, 118.9, 132.9, 163.2, 169.2, 173.2; IR (KBr) 3430, 2935, 1664, 1436, 1383, 1197, 1138 $cm^{-1}$; HRMS calculated for $C_{45}H_{90}N_{15}O_7$ m/z 952.7148, found m/z 952.7139.

Example 2

Preparation of the Formulation

The protein used in the study (IgG1 monoclonal antibody) was stored at 4° C., pH 7.0, at a concentration of 30 mg/ml in a buffer containing 15 mM sodium phosphate, 150 mM NaCl, and 0.1% sodium azide. Sodium azide was used to avoid bacteria contamination.

Protein was dialyzed into the required formulation by performing gel filtration chromatography-based buffer exchange using a Sephadex G-25 resin (GE Healthcare Biosciences, Pittsburgh, Pa., USA) packed into a Tricon™ column (100×10 mm). Concentration of the protein in the samples was measured by UV-VIS spectroscopy at 280 nm using a Spectra Max M2e Multimode Microplate Reader (Molecular Devices, Sunnyvale, Calif., USA) in congruence to the Lambert-Beer Law. Measurement of the concentration of the samples was performed in duplicate and concentration of the concerned buffer was subtracted. In each case, the sample concentration was measured after buffer exchange and the final concentration was adjusted to 5 mg/ml with the respective buffer.

Example 3

Determination of Percentage of Monomer Loss in Formulation at High Temperature

Figure 2:
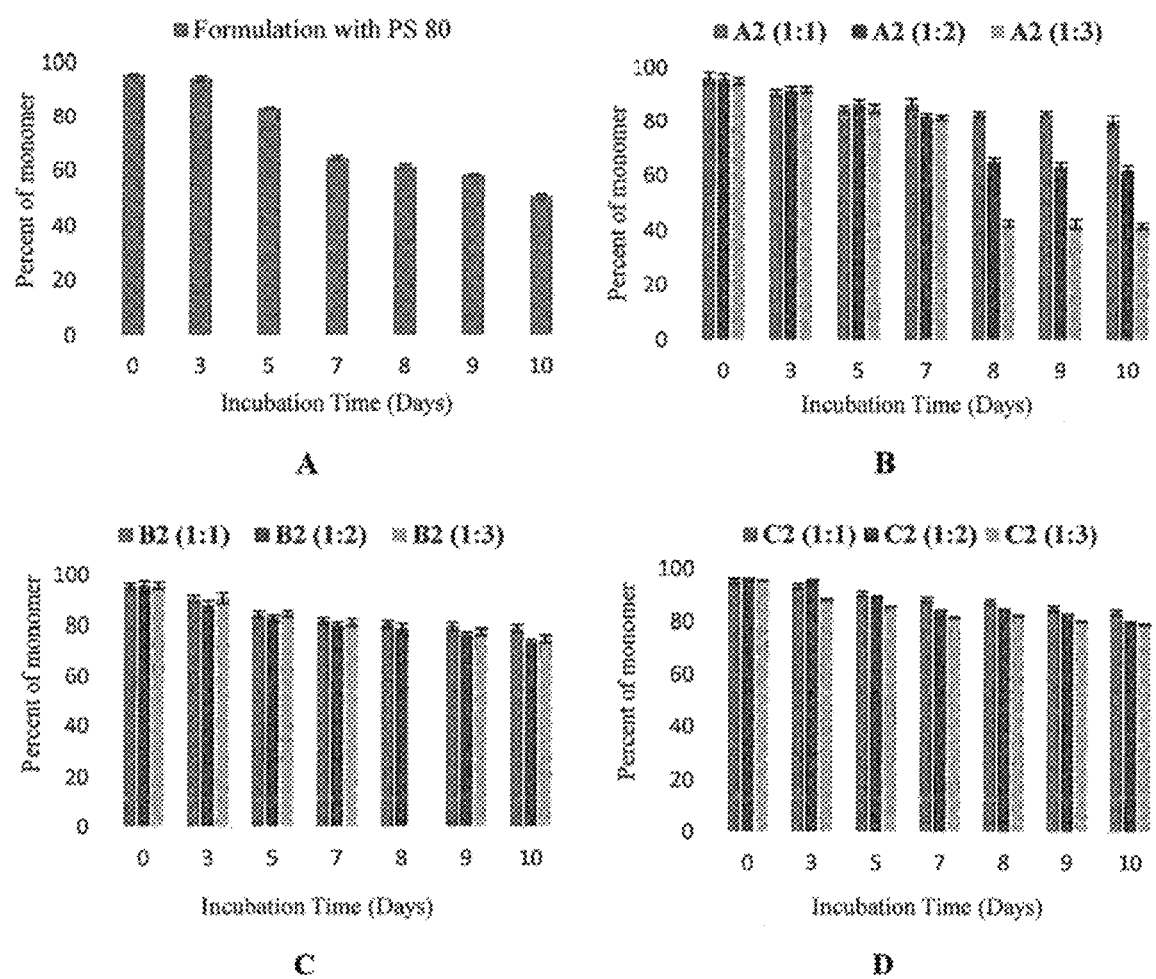
FIG. 2 is a graphical representation of a comparative study carried out to investigate the effectiveness of the lysine based dendrons (A2, B2, and C2) in stabilizing the protein as compared to the stabilization achieved using polysorbate 80 (PS 80).

Various formulations were prepared as described above in Example 2. Dendrons of all three generations (A2, B2, and C2) were used for this purpose. Additionally, ratios of monoclonal antibodies (mAb) to dendrons were also varied. Thus, three formulations were prepared for each dendron (A2, B2, and C2), wherein the ratios of mAb to dendron were 1:1, 1:2, and 1:3. Commercially available mAb formulation containing polysorbate 80 (PS 80, a surfactant, purchased from Merck, India, and used as a 0.02% w/v solution) as an excipient was used for comparative purposes. These formulations were then incubated at a temperature of 55° C. for a period of 10 days. Aliquots were drawn at regular intervals and monomer loss was determined using size exclusion chromatography (SEC-HPLC). With progress of time, the monomer gets converted to aggregates and fragments, resulting in decrease in percentage of monomer and increase in the percentage of aggregates and fragments. These changes were measured by calculating peak area in the SEC chromatogram and a graph was plotted. Higher the percentage of monomer loss, lower was the stabilization provided. The results can be found in FIG. 2. It can be appreciated from the graphs that dendrons of the present invention, when used as excipients, showed drastic improvement in the stabilization of mAb as compared to PS 80. It is evident from the graph that for first 5 days there was not much difference in the stability conferred upon mAb by PS 80 and the dendrons of the present invention. However, with time performance of PS 80 as a stabilizer deteriorated. For first generation dendron, i.e., A2, when the ratio of mAb to dendron was 1:3, the stabilization was only moderate, though it was still comparable to that of PS 80, if not better. However, for second and third generation dendrons, there was a marked difference with regards the extent of stabilization of the mAb, as compared to PS 80. More precisely, the percentage of monomer loss for the formulation containing PS 80 was 3.7 times higher than that for dendrons of the present invention.

Example 4

Aggregation, Fragmentation, and Precipitation Studies

Figure 3:
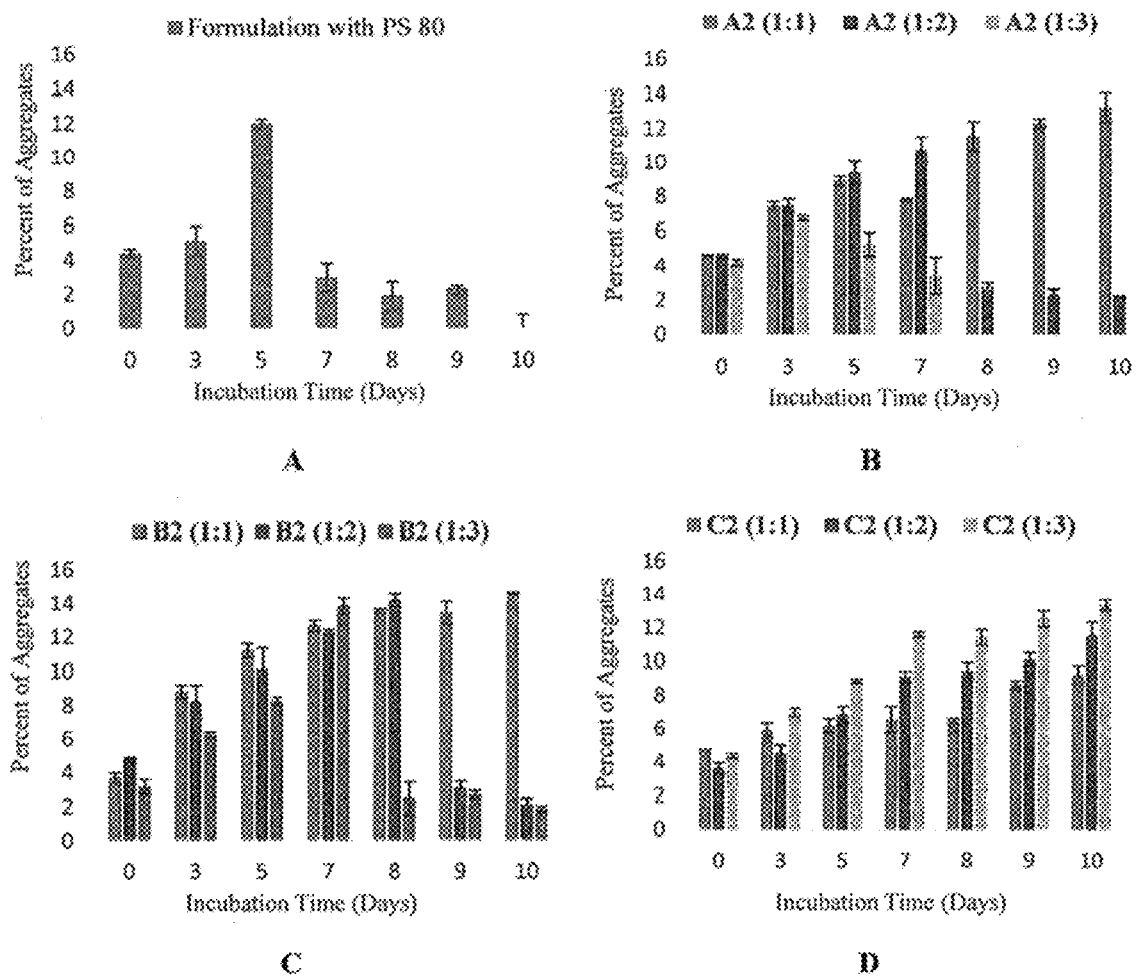
FIG. 3 is a bar graph depicting the trend of aggregate formation in formulation with PS 80 and formulation with A2, B2, and C2 dendrons for 10 days at 55° C.
Figure 4:
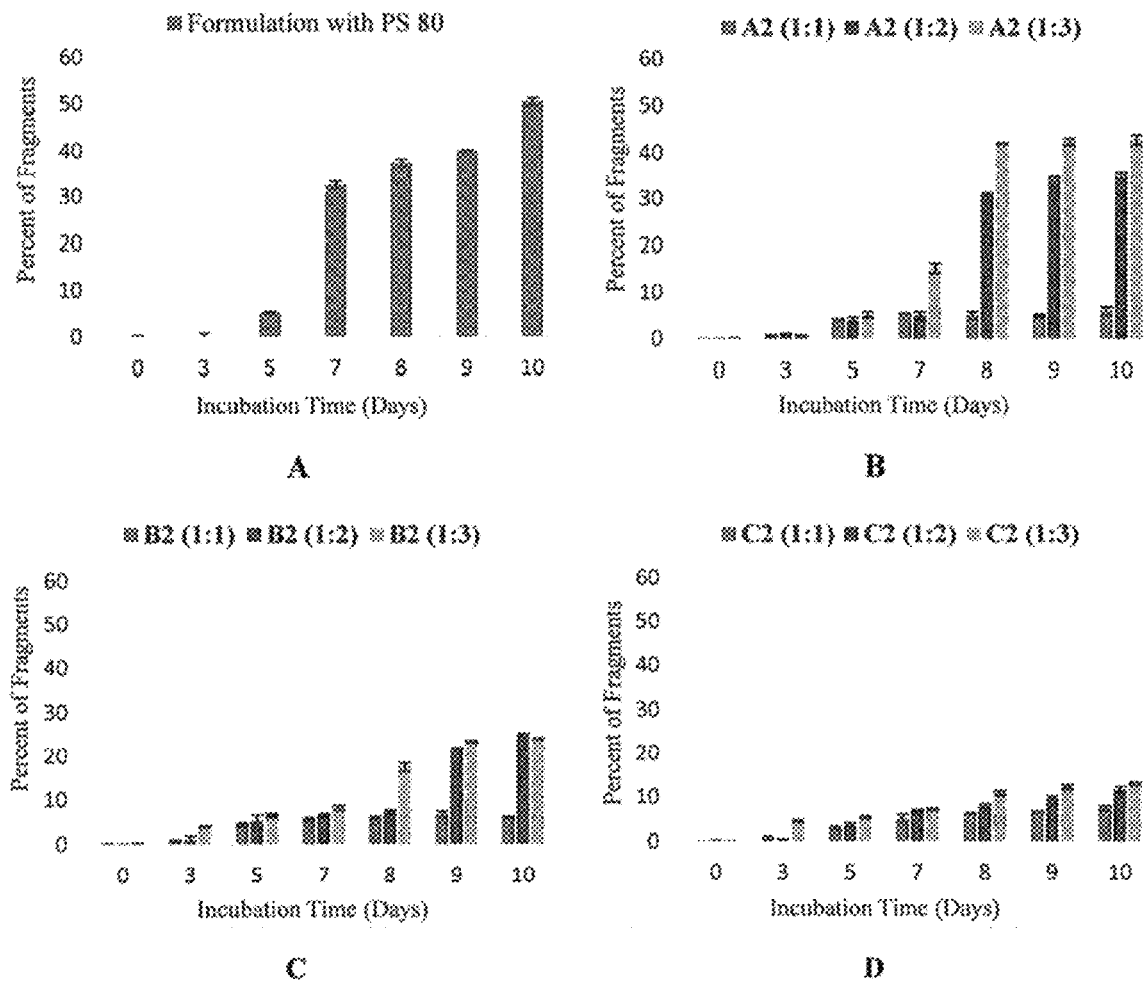
FIG. 4 portrays graphically the trend of fragment formation in formulation with PS 80 and formulation with A2, B2, and C2 dendrons for 10 days at 55° C.
Figure 5:
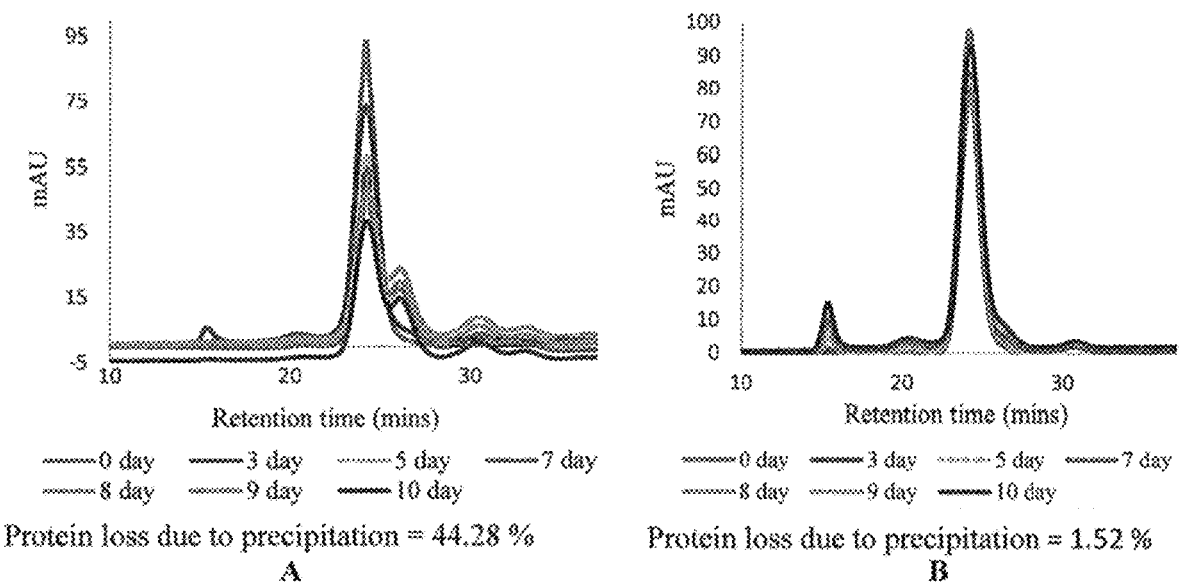
FIGS. 5A and 5B illustrate the overlay of chromatograms of formulation with PS 80 and formulation with C2 (1:1) dendrons respectively.

Further studies were carried out to establish the versatility of the dendrons of instant invention in protecting the mAb from degradation by other modes. Proteins tend to aggregate in the solutions in which they are stored. When the aggregation reaches a certain level, these proteins precipitate out of the solution which is another form of protein degradation. Furthermore, these aggregates, depending upon their stability may fragment into smaller parts. Fragmentation may also take place directly without necessarily having to go through the aggregation stage. This fragmentation is another form of protein degradation and is highly undesirable. Experiments were thus undertaken to investigate the aggregation and fragmentation behavior of the mAb in the formulations of present invention. The formulations used for this purpose were same as those in Example 3. Akin to Example 3, formulation containing PS 80 was also used for comparative purpose. The detailed results are given in FIGS. 3, 4, and 5. FIG. 3 depicts the trend of aggregate formation. One can infer from the graph that the formulations with dendrons of present invention, especially the third generation ones (C2), formed stable aggregates as compared to formulations containing PS 80. It should be noted that this aggregation is not degradative in nature, in that the mAb doesn't precipitate out or fragment further. It is only when the aggregation is not supported by the system that the aggregates precipitate out or fragment into smaller units and the aggregation proves detrimental. The aggregates in formulation containing dendrons of the instant invention were stable enough not to precipitate or fragment; the stability being attributable to the interactions between mAb and dendrons. The difference between the results delivered by formulations containing dendrons of the present invention and those containing PS 80 is more pronounced after fifth day. This underscores the ability of these dendrons to provide stabilization over a prolonged period of time. FIG. 4 portrays the fragmentation behavior of the various formulations. The results are in sync with earlier observations, with the fragmentation for dendron containing formulations, especially C3, being much lower than that for PS 80 formulation. FIG. 5 contains chromatograms for the tested formulations, displaying the precipitation profiles of these formulations. The peaks correspond to mAb concentration in the analyzed sample. Thus, a higher peak implies higher concentration of mAb in the sample and hence lesser precipitation. The difference between the height of peaks for formulations containing dendrons and the ones with PS 80 (especially on the tenth day) therefore amply establishes the superiority of dendrons in stabilizing the mAb. Numerically expressed, the precipitation for PS 80 containing formulation was almost 8.55 times higher than that for dendron containing formulations.

Example 5

Circular Dichroism (CD) Experiments to Study Secondary Structure

Figure 6:
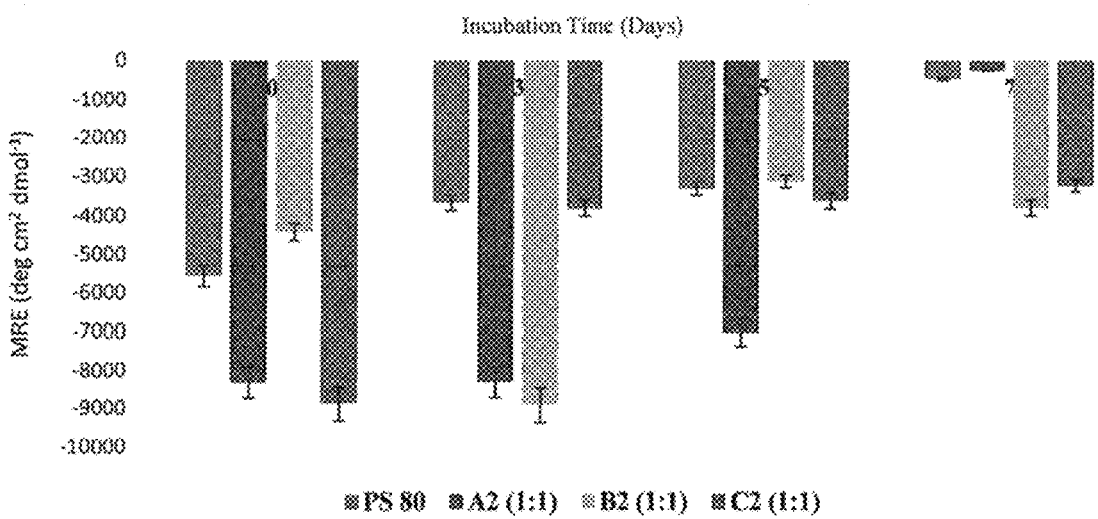
FIG. 6 is a graph representing mean residue ellipticity (MRE) values versus incubation time for formulation with PS 80 and formulation with A2, B2, and C2 dendrons.

With the intent of studying conformational stability of the mAb in formulations, Far-UV CD studies were carried out. Conformational stability is the ability of the protein to retain its secondary structure (alpha helix or beta sheet). mAbs studied in present invention are predominantly beta sheets. Thus, a higher beta sheet content implies a higher conformational stability. FIG. 6 depicts the CD spectrum of different formulations. The observations were recorded at 218 nm. The X-axis represents time, whereas, the Y-axis represents mean residue ellipticity (MRE) values. A dip in CD spectrum signifies higher aggregate content and thus higher beta sheet content. It is apparent from the CD data in FIG. 6 that the formulations containing dendrons of the present invention had a higher amount of mAb in beta sheet structure. This confirms that the secondary structure of the protein is retained to a higher extent in these dendron-containing formulations.

Example 6

Dynamic Light Scattering (DLS) Experiments

Figure 7:
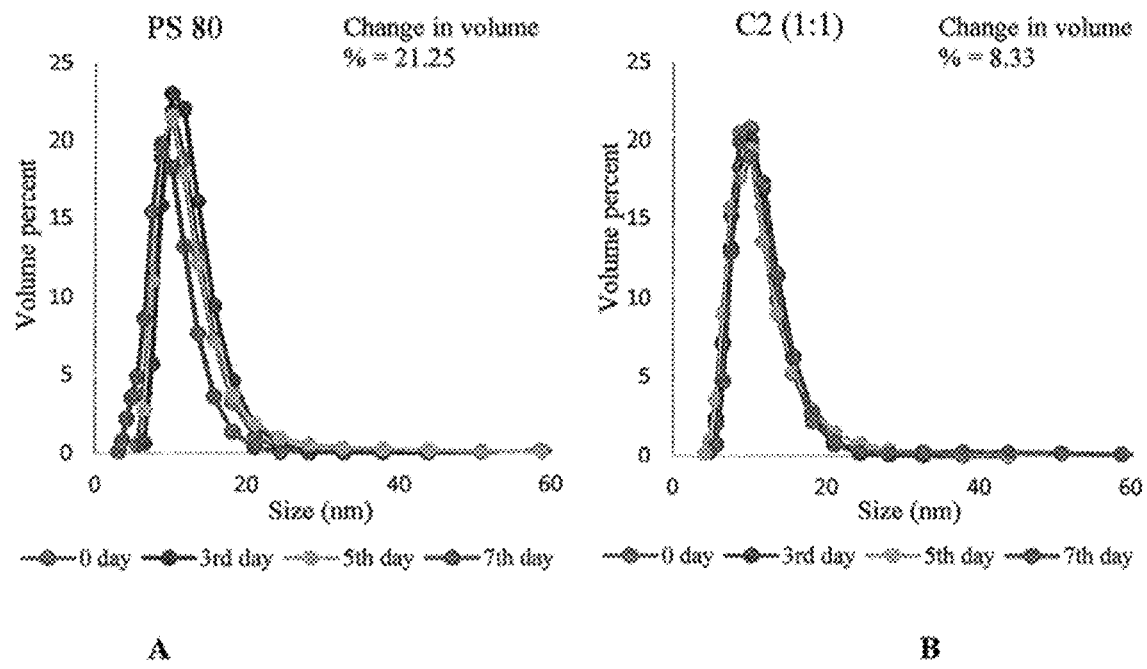
FIGS. 7A and 7B is a line graph representing volume percent versus size (nm) obtained from dynamic light scattering (DLS) for formulation with PS 80 and formulation with C2 (1:1) dendrons respectively.
Figure 8:
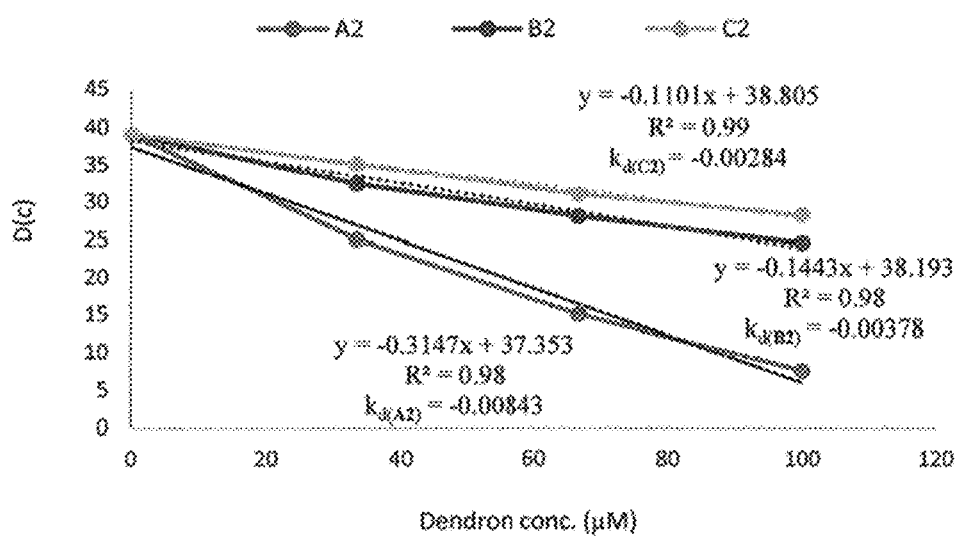
FIG. 8 shows a line graph depicting the diffusion coefficient indicator for protein-protein stability for formulations with dendrons A2, B2, and C2.
Figure 9A:
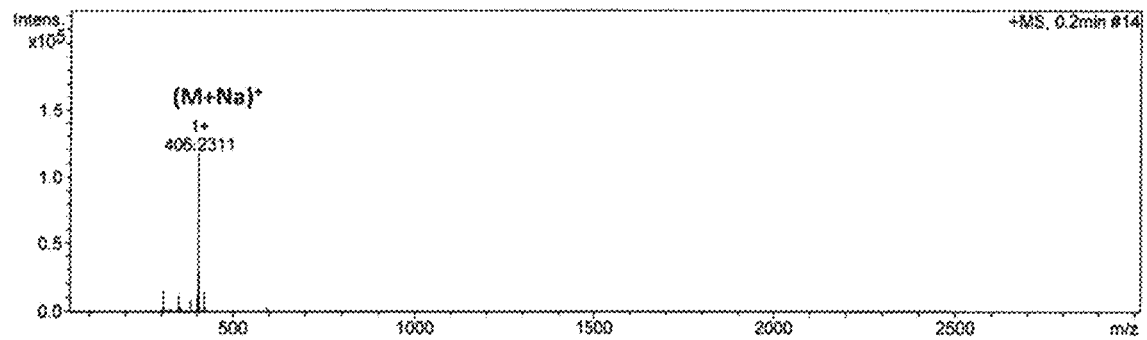
FIG. 9 depicts the HRMS spectra for various dendrons of the invention, namely, (a) A1 (Boc protected dendron of first generation), (b) A2 (deprotected dendron of first generation), (c) B1 (Boc protected dendron of second generation), (d) B2 (deprotected dendron of second generation), (e) C1 (Boc protected dendron of third generation), and (f) C2 (deprotected dendron of third generation).
Figure 9B:
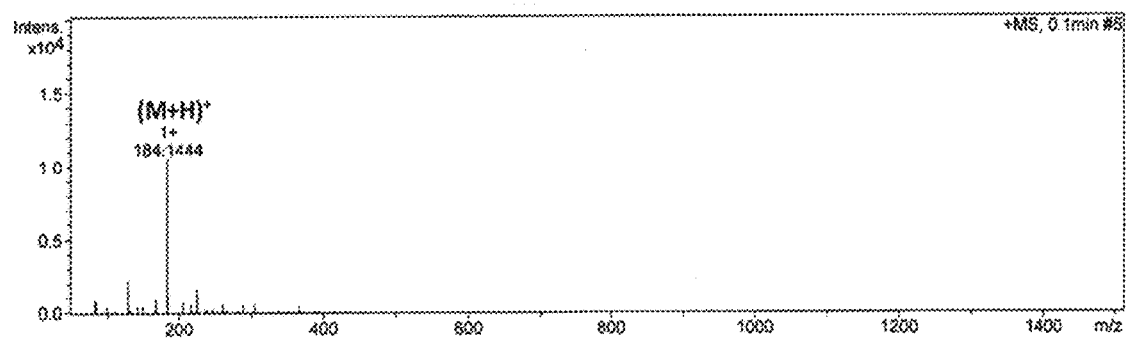
Figure 9C:
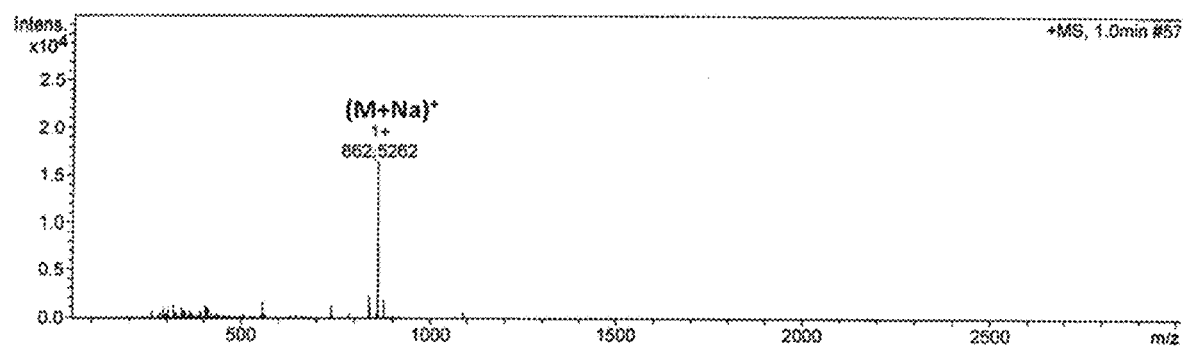
Figure 9D:
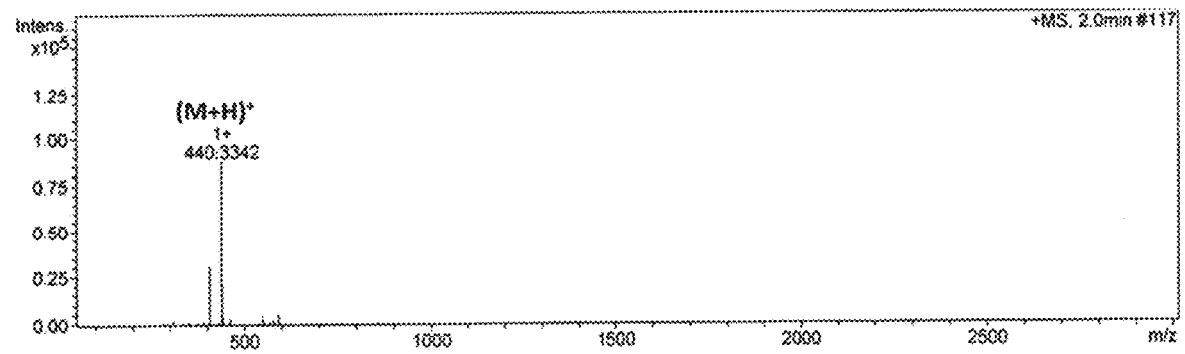
Figure 9E:
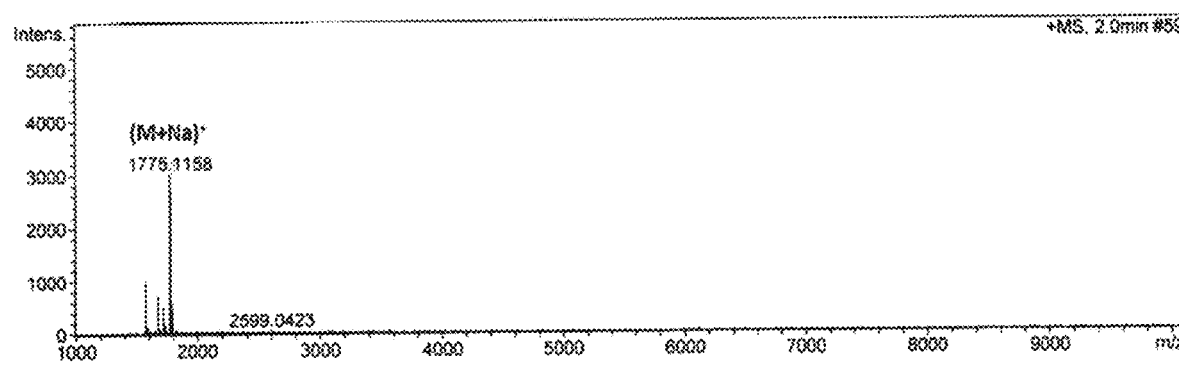
Figure 9F:
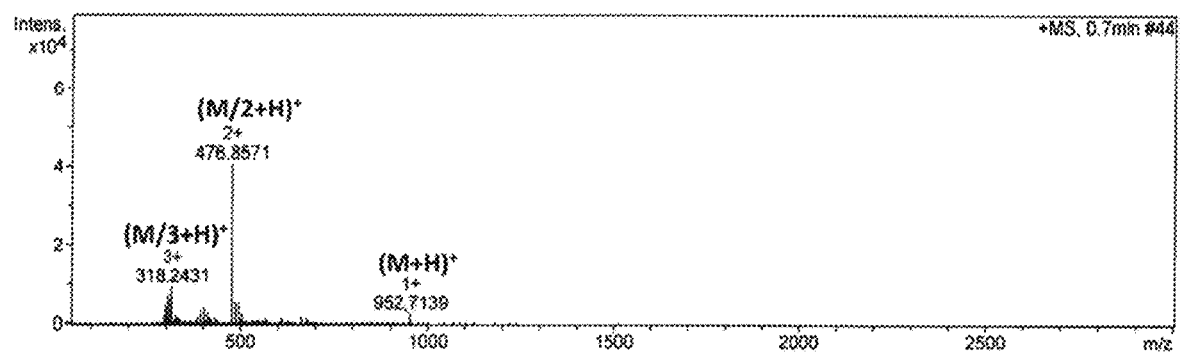
Figure 10:
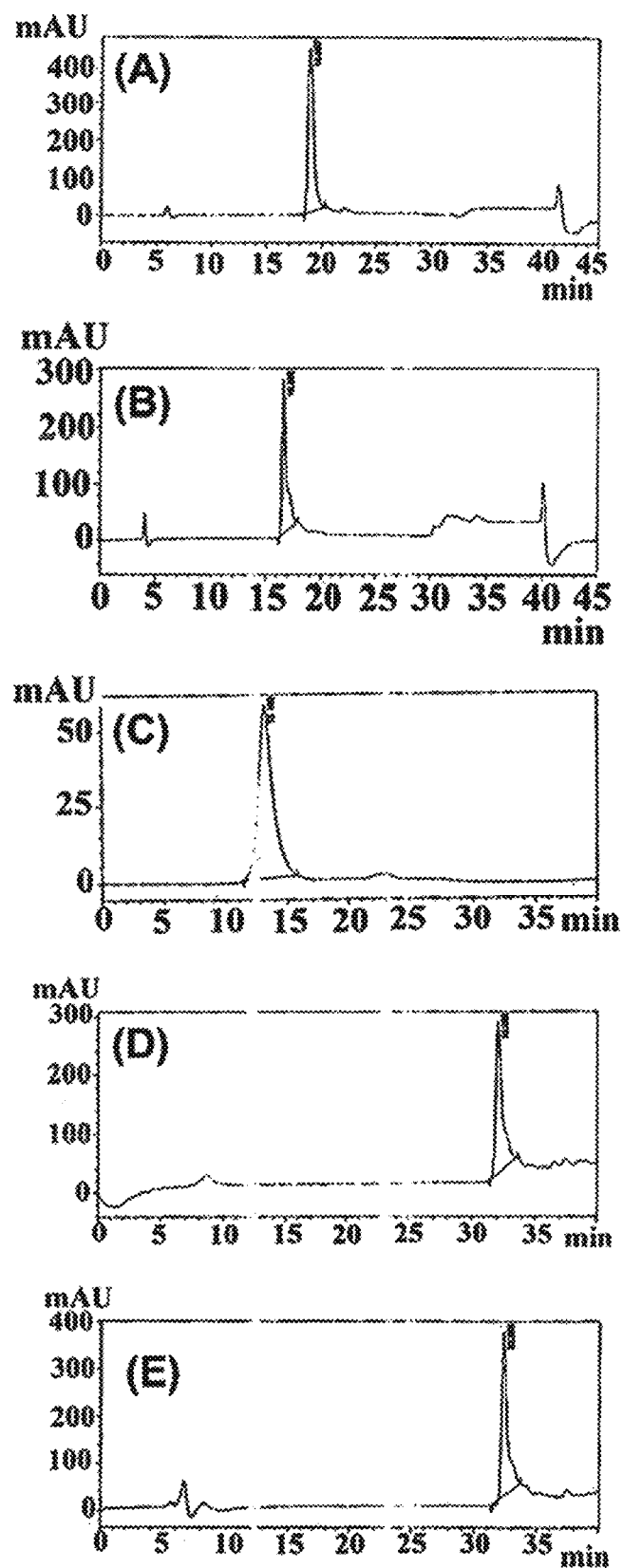
FIG. 10 contains HPLC profiles for dendrons in a binary gradient system (Acetonitrile/Water) using UV detector at 220 nm: (A) A1 (Boc protected dendron of first generation), (B) A2 (deprotected dendron of first generation), (C) B1 (Boc protected dendron of second generation), (D) B2 (deprotected dendron of second generation), (E) C1 (Boc protected dendron of third generation), and (F) C2 (deprotected dendron of third generation).

DLS experiments were further carried out to collect additional data pertaining to the stability of the formulations. FIG. 7 depicts the change in volume shown by various formulations during DLS experiments. DLS is an orthogonal technique which was used to validate the data obtained from SEC-HPLC, described in detail hereinabove. It was observed that formulation with PS 80 exhibited 21.25% change in volume, whereas the same value in case of dendron-based formulations was 8.33%. These volume change data signify that for the formulation with PS 80, the loss in monomer content is more than that for the formulation containing dendron. Further, FIG. 8 represents a graph correlating diffusion coefficient obtained from DLS with protein stability. Higher the $k_d$ value (i.e. a lower negative value), stronger are the repulsive forces amongst protein molecules, and hence less tendency to aggregate. It can be seen from the graph that dendron C2 has the least negative value, indicating its efficiency as an excipient in avoiding undesirable aggregation.

Advantages:
1) The disclosed formulation containing lysine-derived dendrons stabilizes monoclonal antibodies in a far efficient way compared to traditional formulations containing excipients like salts, sugars, amino acids, surfactants, and polymers. The use of amino-acid based dendrons for stabilization of proteins is hitherto unknown.
2) The formulation of present invention protects from degradation induced by both, physical and chemical means.
3) The formulation of the present invention provides unprecedented stabilization against heat induced protein degradation, in that the proteins (mAbs) remained stable in the formulation up to a temperature of 55° C. for 10 days.

Although the subject matter has been described in considerable detail with reference to certain embodiments thereof, other embodiments are possible. As such, the spirit and scope of the invention should not be limited to the description of the embodiments contained herein.

I claim:

1. A formulation comprising:
   a) a dendron of Formula I,

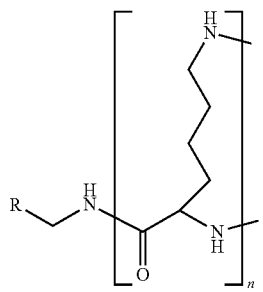

Formula I wherein R is $C_{2-16}$ alkynyl,
wherein 'n' is in the range of 1-15; the branch growth follows a dendritic pattern; all

groups of all repeating units are attached to another repeating unit until the penultimate repeating unit of every branch, and the

groups of the terminal repeating units of all branches are attached to an atom or a functional group independently selected from the group consisting of hydrogen, tert-butyloxycarbonyl (Boc), and fluorenylmethyloxycarbonyl (Fmoc);
   b) at least one bio-therapeutic;
   c) at least one buffer solution; and
   d) at least one salt,
   wherein
   the at least one bio-therapeutic is monoclonal antibodies, and
   the at least one bio-therapeutic to the dendron molar ratio is in the range of 1:0.5-1:3.

2. The formulation as claimed in claim 1, wherein the dendron stabilizes the at least one bio-therapeutic in the formulation at a temperature of up to 55° C.

3. The formulation as claimed in claim 1, wherein the buffer solution is selected from the group consisting of phosphate buffer, citrate buffer, acetate buffer, histidine buffer, succinate buffer, and glycine buffer.

4. The formulation as claimed in claim 3, wherein the buffer solution is phosphate buffer.

5. The formulation as claimed in claim 1, wherein the salt is selected from the group consisting of sodium chloride, potassium chloride, calcium chloride, potassium iodide, magnesium chloride, magnesium sulfate, sodium citrate, and sodium acetate.

6. The formulation as claimed in claim 5, wherein the salt is sodium chloride.

7. The formulation as claimed in claim 1, wherein the formulation has a pH in the range of 5.5-8.

8. The formulation as claimed in claim 1, wherein the dendron has structure as represented by Formula I:

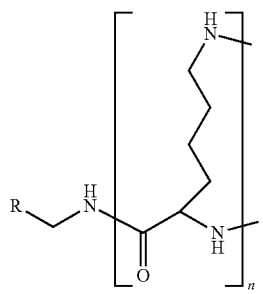

Formula I wherein R is ethynyl,
'n' is in the range of 1-7, the branch growth follows a dendritic pattern; all

groups of all repeating units are attached to another repeating unit till the penultimate repeating unit of every branch, and the

groups of the terminal repeating units of all branches are attached to hydrogen.

9. The formulation as claimed in claim 1, wherein the at least one bio-therapeutic is stabilized by dendron of Formula I and remain stable at high temperatures of up to 55° C. for 10 days.

10. A process for preparing the formulation as claimed in claim 1, comprising the steps of: (a) contacting the at least one buffer solution and the at least one salt with the at least one bio-therapeutic to obtain a mixture; (b) contacting the mixture from step (a) with the dendron of Formula I to obtain the formulation.

11. The process as claimed in claim 10, wherein i) step (a) further comprises at least contacting the at least one buffer solution, the at least one salt, and the at least one bio-therapeutic with at least one anti-bacterial agent selected from the group consisting of sodium azide, thymol, benzalkonium chloride, and glycerol; ii) step (b) is carried out by contacting the mixture from step (a) with the dendron of Formula I using gel filtration chromatography based buffer exchange; and iii) steps (a) and (b) are carried out at a temperature in the range of 20-30° C.

* * * * *